United States Patent
Ansari et al.

(10) Patent No.: US 10,349,896 B2
(45) Date of Patent: Jul. 16, 2019

(54) EPSILON-TUBE FILTER FOR BLUNT NOISE REMOVAL

(71) Applicant: THE REGENTS OF THE UNIVERSITY OF MICHIGAN, Ann Arbor, MI (US)

(72) Inventors: Sardar Ansari, Richmond, VA (US); Kevin Ward, Superior Township, MI (US); Kayvan Najarian, Northville, MI (US)

(73) Assignee: THE REGENTS OF THE UNIVERSTIY OF MICHIGAN, Ann Arbor, MI (US)

( * ) Notice: Subject to any disclaimer, the term of this patent is extended or adjusted under 35 U.S.C. 154(b) by 484 days.

(21) Appl. No.: 14/563,694

(22) Filed: Dec. 8, 2014

(65) Prior Publication Data
US 2016/0249862 A1     Sep. 1, 2016

Related U.S. Application Data

(60) Provisional application No. 61/912,616, filed on Dec. 6, 2013.

(51) Int. Cl.
*A61B 5/00*   (2006.01)
*A61B 5/02*   (2006.01)
(Continued)

(52) U.S. Cl.
CPC .............. *A61B 5/7217* (2013.01); *A61B 5/02* (2013.01); *A61B 5/0295* (2013.01);
(Continued)

(58) Field of Classification Search
CPC .................................................. A61B 5/7217
See application file for complete search history.

(56) References Cited

U.S. PATENT DOCUMENTS

| | | |
|---|---|---|
| 5,603,321 A | 2/1997 | Kynor et al. |
| 5,853,364 A | 12/1998 | Baker et al. |

(Continued)

FOREIGN PATENT DOCUMENTS

EP     2190183     * 12/2010 ............... H04N 5/21

OTHER PUBLICATIONS

Ansari et al., Motion artifact suppression in impedance pneuomgraphy signal for portable monitoring of respiration: an adaptive approach, IEEE J. Biomedical Health Informatics, 11 pp. (Feb. 3, 2016).

(Continued)

*Primary Examiner* — Marc Anthony Armand
(74) *Attorney, Agent, or Firm* — Marshall, Gerstein & Borun LLP

(57) ABSTRACT

The present application describes techniques to filter signals contaminated with blunt noise. Calculated filter coefficients may be applied to signals to generate filtered output signals without the blunt noise. Sets of filter coefficients may be calculated utilizing an ε-tube filter process in conjunction with an autoregressive exogenous (ARX) model. Sets of filter coefficients may be calculated in accordance with a constrained optimization algorithm using data indicative of a source of the blunt noise. When the blunt noise is modeled in accordance with the ARX model, filtered output signals are generated having amplitudes constrained to a selected Epsilon value, which may be the amplitude of a primary component of the unfiltered signal. A set of filter coefficients may be calculated by determining, from the set of filter coefficients that satisfy the constrained optimization algorithm, a solution that produces a filtered output signal having the most time-invariant frequency composition.

24 Claims, 5 Drawing Sheets

(51) Int. Cl.
  A61B 5/08    (2006.01)
  A61B 8/08    (2006.01)
  A61B 5/0295  (2006.01)
  A61B 5/053   (2006.01)
  A61B 5/1455  (2006.01)
(52) U.S. Cl.
  CPC .............. *A61B 5/0535* (2013.01); *A61B 5/08* (2013.01); *A61B 5/14551* (2013.01); *A61B 5/7207* (2013.01); *A61B 8/488* (2013.01); *A61B 8/5269* (2013.01)

(56) References Cited

U.S. PATENT DOCUMENTS

| | | | |
|---|---|---|---|
| 5,924,980 | A | 7/1999 | Coetzee |
| 8,755,877 | B2 | 6/2014 | Zoica |
| 2003/0210047 | A1* | 11/2003 | Mitchell ............ G01R 33/4806 324/309 |
| 2004/0073125 | A1 | 4/2004 | Lovett et al. |
| 2005/0237095 | A1* | 10/2005 | Ando ..................... G01F 15/00 327/172 |
| 2006/0258927 | A1 | 11/2006 | Edgar et al. |
| 2008/0144853 | A1* | 6/2008 | Sommerfeldt ..... G10K 11/1788 381/71.11 |
| 2010/0198097 | A1 | 8/2010 | Takahashi |
| 2010/0310189 | A1* | 12/2010 | Wakazono .............. G06T 5/008 382/258 |
| 2011/0004069 | A1 | 1/2011 | Ochs et al. |
| 2012/0022350 | A1* | 1/2012 | Teixeira ............... A61B 5/0205 600/324 |
| 2013/0324812 | A1 | 12/2013 | Brainard, II et al. |
| 2014/0073958 | A1 | 3/2014 | Rodriguez-Llorente et al. |
| 2015/0065815 | A1* | 3/2015 | Najarian ................ A61B 5/486 600/301 |

OTHER PUBLICATIONS

Asada et al., Active noise cancellation using mems accelerometers for motion-tolerant wearable bio-sensors, Engineering in Medicine and Biology Society, 2004. IEMBS'04. 26th Annual International Conference of the IEEE, vol. 1. pp. 2157-2160 (2004).
Barros et al., Removing artifacts from electrocardiographic signals using independent components analysis, Neurocomputing, 22(1-3):173-86 (1998).
Chan et al., Adaptive reduction of motion artifact from photoplethysmographic recordings using a variable step-size LMS filter, Sensors, 2002, Proceedings of the IEEE, vol. 2, pp. 1343-1346 (2002).
Chawla, PCA and ICA processing methods for removal of artifacts and noise in electrocardiograms: A survey and comparison, Appl. Soft Computing, 11(2):2216-26 (2011).
Hamilton et al., Adaptive removal of motion artifact, Engineering in Medicine and Biology Society, Proceedings of the 19th Annual International Conference of the IEEE, vol. 1, pp. 297-299 (1997).
Hamilton et al., Comparison of methods for adaptive removal of motion artifact, Computers in Cardiology, pp. 383-386 (2000).
Han et al., Development of real-time motion artifact reduction algorithm for a wearable photoplethysmography, Engineering in Medicine and Biology Society, EMBS 2007, 29th Annual International Conference of the IEEE, pp. 1538-1541 (2007).
International Preliminary Report on Patentability, International Application No. PCT/US2014/069124, dated Jun. 7, 2016.
Jeong et al., Development of a technique for cancelling motion artifact in ambulatory ECG monitoring system, ICCIT '08: Third International Conference on Convergence and Hybrid Information Technology, vol. 1, pp. 954-961 (2008).
Khambete et al., Movement artifact rejection in impedance pneumography using six strategically placed electrodes, Physiological measurement, vol. 21, No. 1, p. 79 (2000).
Kim et al., Motion artifact reduction in photoplethysmography using independent component analysis, IEEE Trans Biomedical Engineering, 53(3):566-8 (2006).
Lee et al., Design of filter to reject motion artifact of pulse oximetry, Computer Standards & Interfaces, 26(3):241-9 (2004).
Lee et al., Improved elimination of motion artifacts from a photoplethysmographic signal using a Kalman smoother with simultaneous accelerometry, Physiological Measurement, 31(12):1585 (2010).
Lee et al., Reduction of motion artifacts from photoplethysmographic recordings using a wavelet denoising approach, IEEE EMBS Asian-Pacific Conference on Biomedical Engineering, pp. 194-195 (2003).
Liu et al., Motion artifact reduction in electrocardiogram using adaptive filter, J. Med. Biol. Engineering, 31(1):67-72 (2011).
Luo et al., Experimental study: brachial motion artifact reduction in the ECG, Computers in Cardiology, pp. 33-36 (1995).
Luo et al., The electrode system in impedance-based ventilation measurement, IEEE Trans. Biomedical Engineering, 39(11):1130-41 (1992).
Milanesi et al., Independent component analysis applied to the removal of motion artifacts from electrocardiographic signals, Medical & Biological Engineering & Computing, 46(3):251-61 (2008).
Milanesi et al., Multichannel Techniques for Motion Artifacts Removal from Electrocardiographic Signals, Engineering in Medicine and Biology Society, EMBS '06: 28th Annual International Conference of the IEEE, pp. 3391-3394 (Aug. 30-Sep. 3, 2006).
Rahman et al., An efficient noise cancellation technique to remove noise from the ECG signal using normalized signed regressor LMS algorithm, Bioinformatics and Biomedicine, BIBM '09 IEEE International Conference on IEEE, pp. 257-260 (2009).
Raya et al., Adaptive noise cancelling of motion artifact in stress ECG signals using accelerometer, Engineering in Medicine and Biology, 2002. 24th Annual Conference and the Annual Fall Meeting of the Biomedical Engineering Society EMBS/BMES Conference (IEEE), vol. 2., pp. 1756-1757 (2002).
Reddy et al., Motion artifact reduction in photoplethysmographic signals using singular value decomposition, IMTC 2007: Instrumentation and Measurement Technology Conference Proceedings of, pp. 1-4 (2007).
Reddy et al., Use of Fourier series analysis for motion artifact reduction and data compression of photoplethysmographic signals, IEEE Trans. Instrumentation and Measurement, 58(5): 1706-11 (2009).
Rosell et al., Reduction of motion artifacts using a two-frequency impedance plethysmograph and adaptive filtering, IEEE Trans. Biomedical Engineering, 42(10):1044-8 (1995).
Rosell et al., Signal-to-motion artifact ratio versus frequency for impedance pneumography, IEEE Trans. Biomedical Engineering, 42(3):321-3 (1995).
Sahakian et al., Electrode Motion Artifacts in Electrical Impedance Pneumography, IEEE Trans on Biomedical Engineering, BME-32(6):448-51 (1985).
Seppa et al., Novel electrode configuration for highly linear impedance pneumography, Biomedizinische Technik/Biomedical Engineering, 59(1):35-8 (2013).
Seyedtabaii et al., Kalman filter based adaptive reduction of motion artifact from photoplethysmographic signal, Proceedings of World Academy of Science, Engineering and Technology, vol. 27 (2008).
Tong et al., Adaptive reduction of motion artifact in the electrocardiogram, Engineering in Medicine and Biology, 24th Annual Conference and the Annual Fall Meeting of the Biomedical Engineering Society EMBS/BMES Conference, vol. 2, pp. 1403-1404 (2002).
Wood et al., Low variance adaptive filter for cancelling motion artifact in wearable photoplethysmogram sensor signals, Engineering in Medicine and Biology Society, EMBS 2007, 29th Annual International Conference of the IEEE, pp. 652-655 (2007).
Yan et al., Reduction of motion artifact in pulse oximetry by smoothed pseudo Wigner-Ville distribution, J. Neuroengineering and Rehabilitation, 2(3):1-9 (2005).
Yoon et al., Adaptive motion artifacts reduction using 3-axis accelerometer in E-textile ECG measurement system, J. Med. Systems, 32(2):101-6 (2008).

(56) References Cited

OTHER PUBLICATIONS

Liu et al., Reduction of motion artifacts in electrocardiogram monitoring using an optical sensor, Biomedical Instrumentation & Technology, 2:155-63 (2011).
Ottenbacher et al., Reliable motion artifact detection for ECG monitoring systems with dry electrodes, 30th Annual International IEEE EMBS Conference, Vancouver, British Columbia, Canada, Aug. 20-24, 2008.
Goodyear et al., Filtering noise from fMRI data using the stockwell transform, Proc. Intl. Mag. Reson. Med., 10: (2002).
International Search Report and Written Opinion, International Application No. PCT/US16/18911, dated Jul. 26, 2016.
Ansari et al., "Epsilon-Tube Filtering: Reduction of High-Amplitude Motion Artifacts from Impedance Plethysmography Signal," IEEE Journal of Biomedical and Health Informatics, vol. 19, No. 2, Mar. 2015, pp. 406-417.
International Search Report for International application No. PCT/US2014/069124, dated Sep. 22, 2015.
Written Opinion for International application No. PCT/US2014/069124, dated Sep. 22, 2015.
Ansari et al., "ε-Tube Regression: A New Method for Motion Artifact Reduction," 33rd Annual International Conference of the IEEE EMBS, Boston, MA, Aug. 30-Sep. 3, 2011, pp. 2736-2739.
International Preliminary Report on Patentability, International Patent Application No. PCT/US2016/018911, dated Oct. 3, 2017.

\* cited by examiner

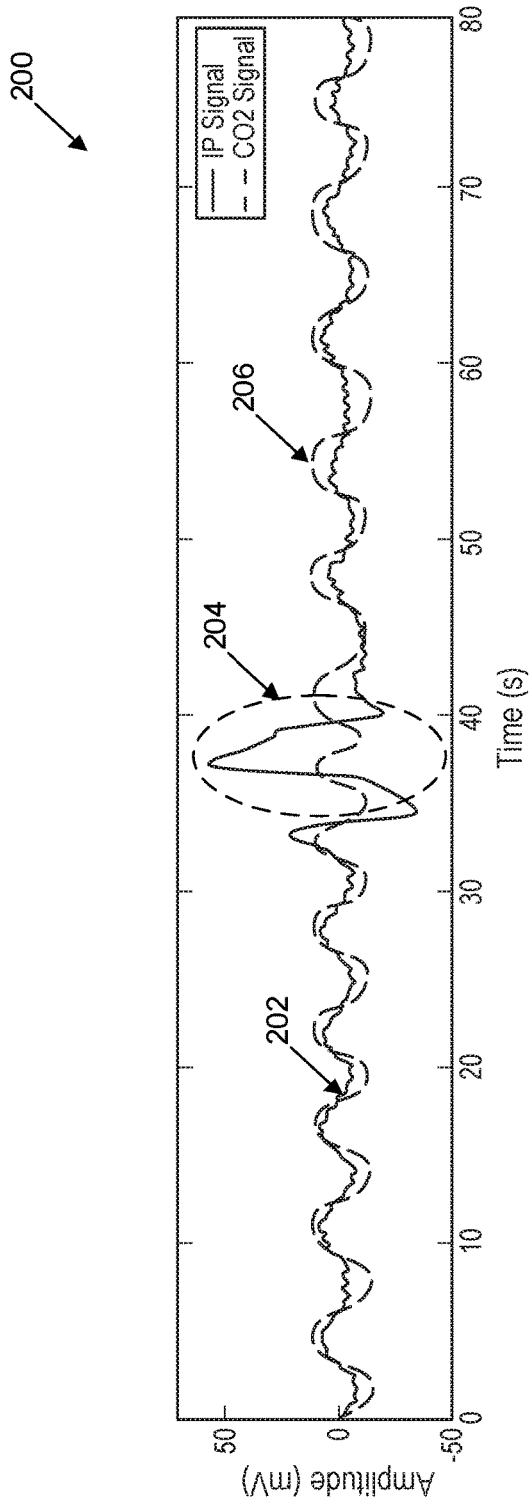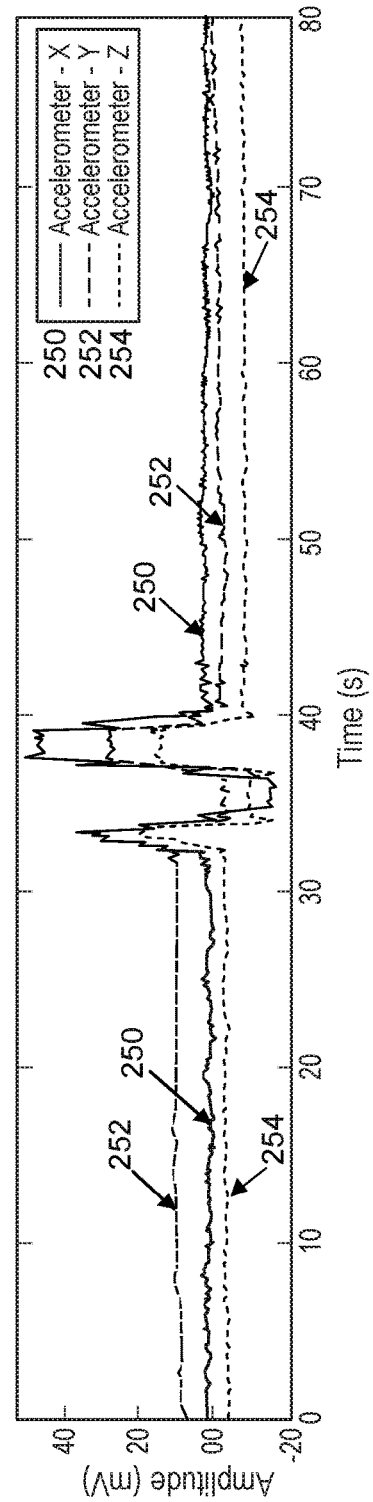
FIG. 2A
FIG. 2B

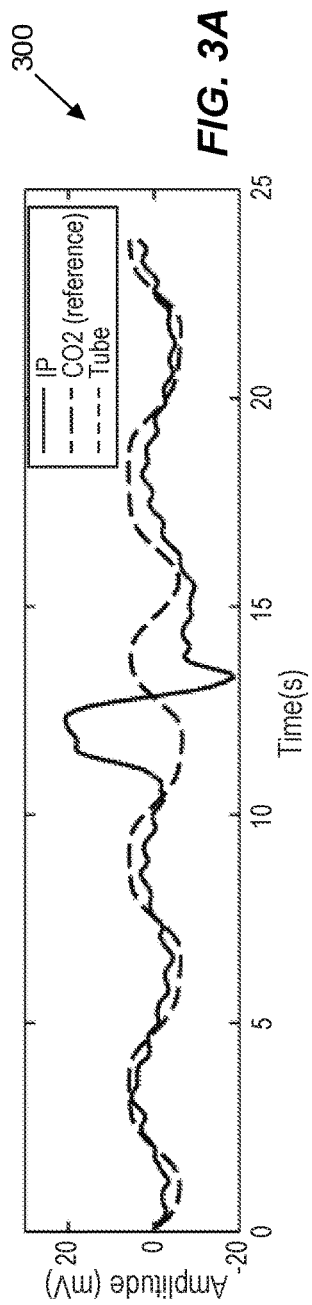
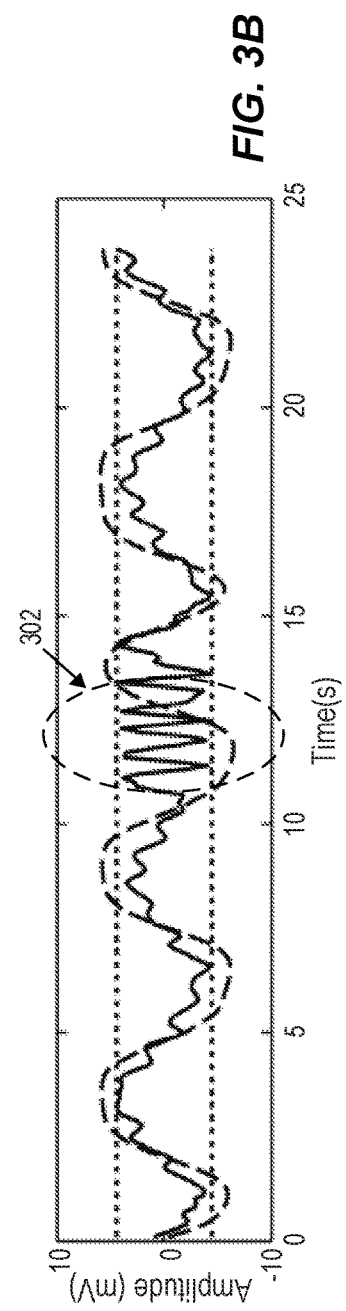
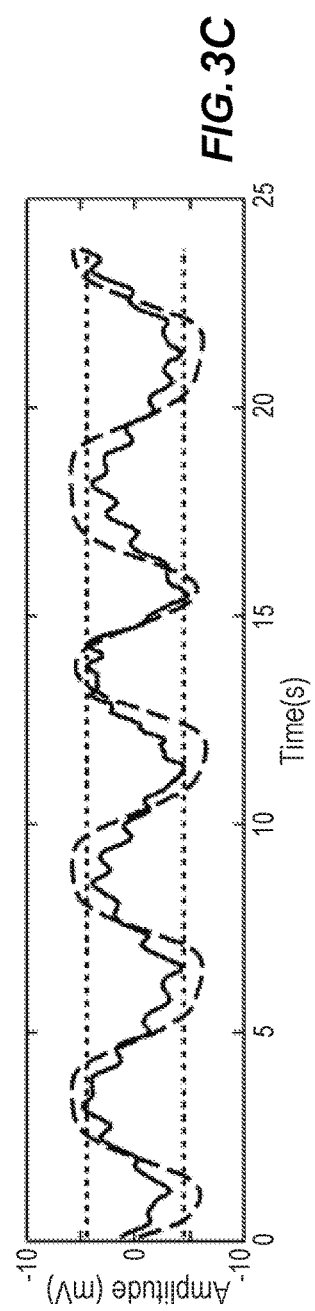
FIG. 3A
FIG. 3B
FIG. 3C

EPSILON-TUBE FILTER FOR BLUNT NOISE REMOVAL

CROSS-REFERENCE TO RELATED APPLICATION

This application claims the priority benefit under 35 U.S.C. § 119(e) of U.S. Provisional Patent Application No. 61/912,616, filed Dec. 6, 2013, the disclosure of which is incorporated herein by reference in its entirety.

STATEMENT OF GOVERNMENTAL INTEREST

This invention was made with government support under W81XWH-09-C-0117, awarded by the U.S. Army/MRMC. The Government has certain rights in the invention.

FIELD OF INVENTION

The present disclosure generally relates to systems, methods, apparatus, and non-transitory media for filtering signals and, more particularly, to filtering signals by removing blunt noise that is mixed with the signals.

BACKGROUND

For patients suffering from a variety of injuries or disease states such venous thrombosis, burns, trauma, various types of heart conditions, sepsis, various types of encephalopathy, dehydration, renal failure, dialysis, hypertension, neuromuscular diseases, low-back pain, motor control disorders, etc., signals generated via relevant medical diagnostic equipment may provide valuable insight for medical professionals.

However, in many medical diagnostic examinations, a diagnostic signal generated by the relevant diagnostic equipment may include noise and/or artifacts. Noise and/or artifacts may be introduced into the diagnostic signal due to a presence of one or more extraneous factors that may influence the diagnostic signal while the test is being performed, such as the patient's movement during the test, electrical noise, etc. Because the noise may have an amplitude larger than the diagnostic signal itself and/or be dynamic or non-repetitive in nature, conventional signal filtering methods may attenuate or distort the diagnostic signal. In addition, conventional attempts to remove artifacts from diagnostic signals using multi-channel recordings of the diagnostic signal may add unwanted complexity, size, and cost to the diagnostic equipment.

As a result, performing signal filtering with portable diagnostic equipment to remove artifacts while recovering the signal of interest presents several challenges.

SUMMARY

The present application describes techniques to filter signals having mixed blunt noise, which may be characterized as noise having relatively high amplitudes and low frequencies having a frequency spectrum that overlaps with that of the signal of interest. Filtering may be accomplished using a two-step process to implement an Epsilon-tube (ε-tube) filter.

First, an autoregressive exogenous (ARX) model may be used to generate blunt noise models using sets of filter coefficients applied to data associated with the source of the blunt noise. When the ARX models are subtracted from the original signal using sets of filtering coefficients, the filter provides a set of potential filtered output signals having corresponding filter coefficient solutions that satisfy a constrained optimization algorithm. This optimization algorithm ensures that the filter coefficient solutions result in filtered signals having a maximum amplitude (the ε-tube) equal to (or nearly equal to) that of the diagnostic signal.

Second, a filter coefficient solution may be selected from the solutions satisfying the constrained optimization algorithm by selecting the filtered output signal having most "regular" solution. Signal regularity may be determined by analyzing the filtered output signals in the frequency domain to determine the filter coefficient solution that has the most time-invariant frequency composition. In one example, a Stockwell-transform algorithm may be utilized to implement this determination. In this way, the two-step ε-tube filtering process avoids issues associated with conventional filtering methods, such as modeling the diagnostic signal of interest as well as the artifacts and/or the introduction of distortion into the filtered output signal.

In an example, a method includes one or more processors applying a selected set of filter coefficients having a frequency composition that is the least frequency-varying of the plurality of filtered signals that satisfy an Epsilon constraint.

BRIEF DESCRIPTION OF THE DRAWINGS

The figures described below depict various aspects of the system and methods disclosed herein. It should be understood that each figure depicts an aspect of a particular aspect of the disclosed system and methods, and that each of the figures is intended to accord with a possible aspect thereof. Further, wherever possible, the following description refers to the reference numerals included in the following figures, in which features depicted in multiple figures are designated with consistent reference numerals.

FIG. 2A illustrates a graphical representation of an IP signal contaminated with blunt noise;

FIG. 2B illustrates a graphical representation of a accelerometer signals corresponding to the source of the blunt noise shown in FIG. 2A;

FIG. 3A illustrates a graphical representation of an IP signal contaminated with blunt noise and a reference $CO_2$ signal;

FIG. 3B illustrates a graphical representation of a filtered IP signal after ε-tube filtering;

FIG. 3C illustrates a graphical representation of a filtered IP signal after application of ε-tube filtering as shown in FIG. 2B and application of regularization;

DETAILED DESCRIPTION

Figure 1:
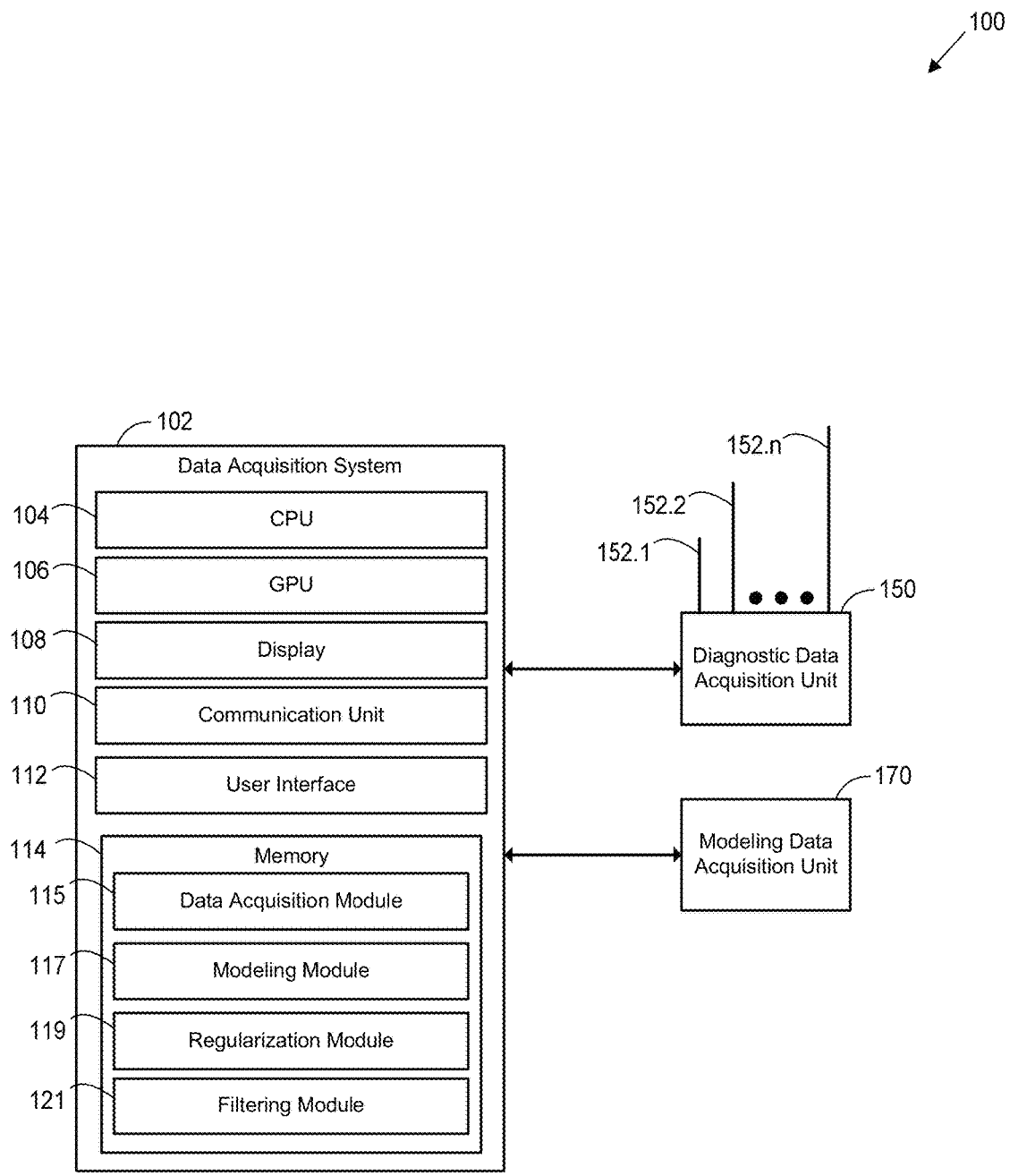
FIG. 1 illustrates a block diagram of an exemplary system 100 in accordance with an exemplary aspect of the present disclosure.

The present application describes various embodiments in the context of techniques using diagnostic systems to generate, measure, receive, sample, analyze, process, and/or filter one or more diagnostic signals. These diagnostic systems may include those used to non-invasively or invasively monitor one or more biological processes for a patient undergoing a test procedure. For example, diagnostic systems may be used monitor changes in the volume of blood in the venous system of patients. Such techniques may utilize an impedance plethysmography system as one example, but may also include any suitable type of diagnostic system such as photoplethysmography, electromyography, ultrasound, etc.

Furthermore, the embodiments described herein are applicable to any suitable type of system having periodic signals that may be prone to noise contamination. In various embodiments, this may include medical or non-medical diagnostic systems. For example, the filtering methods described herein may be applied to medical diagnostic systems configured to generate, measure, receive, sample, analyze, process, and/or filter signals associated with electrocardiograms, impedance cardiography, arterial blood pressure waveforms, venous blood pressure waveforms, intracranial pressure waveforms, photoplethysmography waveforms, end-tidal carbon dioxide waveforms, Doppler signals, piezoelectric signals, etc.

To provide additional examples, the filtering methods described herein may also be applied to non-medical diagnostic systems configured to generate, measure, receive, sample, analyze, process, and/or filter signals associated with exercise equipment, biometric sensors, fitness trackers, wearable electronic devices, etc.

Impedance Plethysmography and Respiratory Rate

The various embodiments explained herein often refer to impedance plethysmograph (IP) signals as illustrative examples, but these embodiments are equally applicable to any suitable type of electrical signal that may be adequately sampled and filtered in accordance with the techniques presented herein. A brief explanation of impedance plethysmographs is presented below for clarity.

Conventionally, impedance plethysmographs (IPs) may be used to determine changes in blood volume within portions of a patient's limb, which is particularly useful in diagnosing conditions such as venous thrombosis. Impedance plethysmographs typically function by injecting a high-frequency, low amplitude sinusoidal current into a segment of interest using a pair of skin electrodes, or current electrodes. Another pair of electrodes is also used to measure an imposed voltage difference between the current injection points, which is caused by the passage of electrical current through the patient's tissue. A diagnostic signal, in this case an IP signal, may then be generated based upon a ratio between the measured voltage and the injected current. Because the electrical conductivity of the tissue is mainly influenced by the volume of blood in that region, variations of the measured voltage (and thus variations in the impedance) cause the IP signal to reflect variations caused by the blood's electrical conductivity in the segment of interest due to changes in blood volume.

One of the main sources of blood volume variation and tissue movement, in particular in the chest and abdomen area, is respiration. As a result, the respiratory signal and the respiratory rate may be extracted from an IP signal acquired from the thorax and abdomen area when the subject is motionless. However, a patient's movement is also a large source of blood volume variation. As a result, a patient's movement during an administered IP test may result in drastic variations in the measured IP signal resulting in blunt noise, in this case "motion artifacts" (MA) having amplitudes larger than the amplitude of the respiratory component of the IP signal. As a result, it is desirable to use filtering methods to eliminate the MA's before the signal is used for monitoring respiration.

FIG. 1 illustrates a block diagram of an exemplary system 100 in accordance with an exemplary aspect of the present disclosure. System 100 may include a data acquisition system 102, a diagnostic data acquisition unit 150, n number of electrodes 152.1-152.$n$, and a modeling data acquisition unit 170.

Diagnostic data acquisition unit 150 may be implemented as any suitable type of diagnostic device configured to receive signals via electrodes 152.1-152.$n$. Depending on the particular type of test that is performed, diagnostic data acquisition unit 150 may be implemented as one or more types of diagnostic devices. Diagnostic data acquisition unit 150 may be configured to receive signals via electrodes 152.1-152.$n$, to process these signals, and/or to send the signals received via electrodes 152.1-152.$n$ and/or the processed signals to data acquisition system 102. In one example, diagnostic data acquisition unit 150 may be part of a Biopac system, such as the Biopac EBI100C electrobioimpedance amplifier, manufactured by Biopac Systems, Inc. of Aero Camino Goleta, Calif.

Electrodes 152.1-152.$n$ may be configured as any suitable type of device to measure, monitor, and/or generate electrical signals based upon their location on a test subject and/or the type of test being performed via diagnostic data acquisition unit 150. For example, if diagnostic data acquisition unit 150 is implemented as the EBI100C electrobioimpedance amplifier, then electrodes 152.1-152.$n$ may be configured in accordance with a system that is compatible with such a system. To provide another example, if diagnostic data acquisition unit 150 is used to conduct an IP test, some of electrodes 152.1-152.$n$ may be configured as current injecting electrodes while some of electrodes 152.1-152.$n$ may be configured as voltage monitoring electrodes. Thus, electrodes 152.1-152.$n$ may provide diagnostic data acquisition unit 150 with the appropriate signals to generate one or more IP signals and/or to send the IP signals to data acquisition system 102.

Electrodes 152.1-152.$n$ may be placed in any suitable location to provide signals in accordance with the type of application and/or the test being conducted. For example, if an electrocardiography (ECG) measurement is performed, one or more of electrodes 152.1-152.$n$ may be placed on a suitable portion of a patient's chest. To provide another example, if an IP test is performed, one or more of electrodes 152.1-152.$n$ may be placed on a suitable portion of the patient commensurate with an IP test, such as between the patient's third and tenth ribs, a traditional trans-thoracic electrode placement, etc.

Modeling data acquisition unit 170 may be configured to measure, generate, receive, and/or monitor one or more data signals associated with the source of noise introduced into the diagnostic signal measured by diagnostic data acquisition unit 150. Modeling data acquisition unit 170 may be implemented as any number and/or type of sensors based upon the source of the noise introduced into the diagnostic signal that is to be modeled.

In an embodiment, the noise may include, for example, blunt noise. In embodiments in which the blunt noise takes the form of MAs, modeling data acquisition unit 170 may be implemented as one or more sensors configured to monitor the patient's movement. Some examples of these types of sensors may include accelerometers, pressure sensors, piezoelectric sensors, etc. To provide an illustrative example, modeling data acquisition unit 170 may be implemented as a three-axis accelerometer configured to measure acceleration in the x, y, and z-axes. Modeling data acquisition unit 170 may be worn by and/or attached to a patient such that these accelerometer signals represent one or more movement parameter values indicative of the patient's movement in each of the x, y, and z-axes. Modeling data acquisition unit 170 may be configured to transmit the acceleration signals and/or one or more movement parameter values to data acquisition system 102.

Data acquisition system 102 may include a central processing unit (CPU) 104, a graphics processing unit (GPU) 106, a display 108, a communication unit 110, a user interface 112, and a memory 114. In various embodiments, data acquisition system 102 may be implemented as any suitable computing device, such as a smartphone, a mobile device, a tablet computer, a laptop computer, a dedicated diagnostic system, a personal computer, a wearable computing device, etc.

In some embodiments, data acquisition system 102 may be implemented as a single device, for example, as shown in FIG. 1. Such implementations may be particularly useful when a portable and/or mobile device is desirable. In other embodiments, data acquisition system 102 may be implemented as a device that may perform functions of two or more devices, such as a device that may perform functions of both data acquisition system 102 and diagnostic data acquisition unit 150, for example. Such implementations may be particularly useful when it is desirable to modify an existing off-the-shelf system to perform the embodiments as described herein, for example, by performing a software and/or firmware upgrade, by adding specialized hardware cards or modules, etc.

Display 108 may be implemented as any suitable type of display and may facilitate user interaction in conjunction with user interface 112, such as a mobile device display, a smartphone display, a capacitive touch screen display, a resistive touch screen display, etc. In various aspects, display 108 may be configured to work in conjunction with CPU 104 and/or GPU 106 to display one or more diagnostic signals received and processed by communication unit 110 and/or filtered by CPU 104 executing instructions in one or more modules stored in memory 114.

Communication unit 110 may be configured to process, send signals to, and/or receive signals from diagnostic data acquisition unit 150 and/or modeling data acquisition unit 170. Communication unit 110 may be configured to communicate with diagnostic data acquisition unit 150 and/or modeling data acquisition unit 170 in accordance with any suitable type and/or number of wired and/or wireless communication protocols.

User interface 112 may be configured to receive user-input and to facilitate user interaction with data acquisition system 102. For example, user-interface 112 may be implemented as a "soft" keyboard that is displayed on display 108, an external hardware keyboard communicating via a wired or a wireless connection (e.g., a Bluetooth keyboard), an external mouse, or any other suitable user-input device.

User-interface 112 may include a microphone configured to receive user input in the form of voice input, such as voice commands, for example. In some aspects, voice commands received via user interface 112 may be converted to text, for example, via CPU 104. In this way, user interface device 112 may allow a user to enter text in lieu of typing. User interface 112 may facilitate a user adjusting, modifying, changing, etc., one or more options or settings of data acquisition system 102 depending on a particular implementation. For example, a user may utilize user interface 112 to change display settings, to change one or more design parameters used in the signal filtering process as further discussed below, etc.

CPU 104 and/or GPU 106 may be configured to communicate with memory 114 to store to and read data from memory 114. In accordance with various embodiments, memory 114 is a computer-readable non-transitory storage device that may include any combination of volatile (e.g., a random access memory (RAM), or a non-volatile memory (e.g., battery-backed RAM, FLASH, etc.). Memory 114 may be configured to store instructions executable on CPU 104 and/or GPU 106. These instructions may include machine-readable instructions that, when executed by CPU 102 and/or GPU 106, cause CPU 102 and/or GPU 106 to perform various acts.

Data acquisition module 115, modeling module 117, regularization module 119, and filtering module 121 are portions of memory 114 configured to store instructions executable by CPU 104 and/or GPU 106. In accordance with various embodiments, any of data acquisition module 115, modeling module 117, regularization module 119, and/or filtering module 121 may operate as a separately executable software application, a plugin that extends the functionality of another software application such as a web browser, an application programming interface (API) invokable by a software application, etc. The instructions included within any of any of data acquisition module 115, modeling module 117, regularization module 119, and/or filtering module 121 may be compiled and executable on CPU 104 and/or GPU 106 directly, or not compiled and interpreted by the CPU 104 and/or GPU 106 on a runtime basis.

Data acquisition module 115 may include instructions that, when executed by CPU 104 and/or GPU 106, causes CPU 104 and/or GPU 106 to receive, store, and/or process data received from diagnostic data acquisition unit 150 and/or modeling data acquisition unit 170 via communication unit 110. In various embodiments, this data may include, for example, sampled data representative of signals received from diagnostic data acquisition unit 150 over one or more processing windows, data representative of signals received from modeling data acquisition unit 170 over one or more processing windows, etc.

Modeling module 117 may include instructions that, when executed by CPU 104 and/or GPU 106, causes CPU 104 and/or GPU 106 to retrieve data stored by data acquisition module 115 and to utilize this data to construct one or more models of blunt noise that may be mixed with the signals received by diagnostic data acquisition unit 150 over one or more processing windows. The instructions stored in modeling module 117 may facilitate CPU 104 and/or GPU 106 to construct blunt noise models using any suitable type of modeling process or algorithm, such as tangent sigmoid activation functions, autoregressive exogenous models, etc.

In various embodiments, modeling module 117 may include instructions to facilitate the modeling of blunt noise using the sampled data measured by modeling data acquisition unit 170, which may be indicative of the source of the blunt noise. In embodiments in which the blunt noise is caused by a patient's movement, modeling module 117 may include instructions to construct models using one or more movement parameter values, which may include one or more accelerometer signal values. The techniques represented by the instructions to construct models are further discussed in detail below.

As will be discussed below in further detail, one or more blunt noise models may be constructed based upon sets of filter coefficients that may be applied to the sampled data measured by modeling data acquisition unit 170 to attempt to estimate the blunt noise. To filter the signal contaminated with blunt noise, the original contaminated signal may be filtered according to one or more sets of filter coefficients such that the blunt noise model is subtracted from the original signal to produce a filtered signal. To avoid distortion of the filtered signal, an ε-tube value is used to constrain the calculated filter coefficients to those solutions that provide filtered signal amplitudes having amplitudes less than the amplitude of the primary component of the original contaminated signal.

In this way, modeling module 117 includes instructions to facilitate the calculation of sets of filter coefficient solutions by CPU 104 and/or GPU 106 that produce filtered signals having amplitudes that are "clamped" by the ε-tube. Because several sets of filter coefficients may satisfy this constraint, additional calculations, which are further discussed below, may be used to further narrow the filter coefficient solution.

In some embodiments, modeling module 117 may include instructions to set one or more values, such as the Epsilon value and/or other modeling parameters to be further discussed below, based upon characteristics of the measured signal such as amplitude, frequency, etc. In other embodiments, modeling module 117 may include instructions to allow a user to specify these values, for example, via user interface 112

Regularization module 119 may include instructions that, when executed by CPU 104 and/or GPU 106, causes CPU 104 and/or GPU 106 to select one of the sets of filter coefficients, from those that satisfy the ε-tube constraint, which yields a filtered signal having a frequency composition that is the least frequency-varying of the solutions. The instructions stored in regularization module 119 may facilitate CPU 104 and/or GPU 106 to select a filtering solution using any suitable type of frequency transform and/or algorithm, such as a Stockwell-Transform, for example, as further discussed below.

Filtering module 121 may include instructions that, when executed by CPU 104 and/or GPU 106, causes CPU 104 and/or GPU 106 to store and/or process data used in conjunction with the overall filtering process implemented by data acquisition system 102 in accordance with the embodiments as described herein. For example, filtering module 121 may store, as part of its instructions, data such as defined filter design variables, sliding time window scales, processing windows and/or sliding windows, design constraints, one or more filter parameters, defined slack variables, user selections, filter coefficients, ε-tube values, and/or predetermined constants used by data acquisition system 102 to filter diagnostic signals. To provide another example, filtering module 121 may include instructions that, when executed by CPU 104 and/or GPU 106, causes CPU 104 and/or GPU 106 to apply the filter coefficient solutions to the diagnostic signals, to perform diagnostic signal filtering in real-time and/or as part of one or more batch processes after the diagnostic signal has been sampled and stored in memory 114.

In some embodiments, filtering module 121 may include instructions that cause CPU 104 and/or GPU 106 to work in conjunction with user interface 112, for example, to receive data used in conjunction with the overall filtering process. In this way, a user may originally program the instructions stored in filtering module 121, for example, and later overwrite these instructions to update the data.

In other embodiments, filtering module 121 may include instructions that cause CPU 104 and/or GPU 106 to work in conjunction with communication unit 110, for example, to set one or more data values used in the filtering process, such as the Epsilon value and/or other modeling parameters to be further discussed below, based upon characteristics of the measured signal such as amplitude, frequency, etc.

FIG. 2A illustrates a graphical representation of an IP signal contaminated with blunt noise. In an embodiment, IP signal 202 may be measured via one or more of electrodes 152.1-152.$n$ and sampled and/or processed by diagnostic data acquisition unit 150. Again, IP signal 202, or data samples representative thereof, may be received by data acquisition system 102 via, for example, communication unit 110.

The embodiments described herein may be applicable to filter any suitable type of periodic signal, but IP signal 202 is shown in FIG. 2A for illustrative purposes. In addition to IP signal 202, FIG. 2A also includes a $CO_2$ signal 206 for comparative purposes. Because IP signals measure changes in blood volume over a measure portion of a patient's body, a large contributor to these volumetric changes is the patient's breathing. Another contributing factor to blood volume changes is the patient's heart rate, which can also be observed as the high frequency ripple present throughout IP signal 202. $CO_2$ signal 206 is not needed for the filtering process, but shows how IP signal 202 tracks the patient's breathing rate. The primary portion of IP signal 202 that tracks the patient's respiratory rate, therefore, is often referred to as the respiratory component of IP signal 202.

IP signal 202 also includes blunt noise 204. In this example, blunt noise 204 may be associated with a motion artifact caused by the patient's movement, resulting in a sudden change in blood volume. As shown in FIG. 2A, blunt noise 204 has an amplitude greater than the respiratory component of IP signal 202 and a relatively low frequency.

FIG. 2B illustrates a graphical representation of accelerometer signals corresponding to the source of the blunt noise shown in FIG. 2A. Assuming that blunt noise 204 corresponds to a MA, the accelerometer signals for each of the x, y, and z axes as shown in FIG. 2B may indicate the source of the MA, which is indicated by the correlation in time between blunt noise 204 and the variations in the accelerometer values in FIGS. 2A and 2B. In an embodiment, the accelerometer signals shown in FIG. 2B may be measured, sampled, and/or processed by modeling data acquisition unit 170 via one or more of appropriate accelerometer sensors attached to the patient while the IP test is being performed. The accelerometer signals shown in FIG. 2B, or data samples representative thereof, may also be received by data acquisition system 102 via, for example, communication unit 110. In an embodiment, the data sample values for each of the accelerometer signals at each sampling point within a processing window may be stored as movement parameter values in a suitable portion of memory 114. As will be further explained below in mathematical terms, these movement parameter values may be represented as vector representations to determine an appropriate set of filter coefficient solutions that, when used to filter the contaminated IP signal 202, may remove MA 204 from IP signal 202.

ε-Tube and Autoregressive Exogenous Models

The ε-tube filter process refers to filtering using a defined error term, ε, which ensures the filtered signal is constrained within a "tube," or amplitude, set by ε. CPU 104 and/or GPU 106 may execute instructions stored in modeling module 117 to calculate one or more sets of filter coefficients, which may be applied to an input signal via CPU 104 and/or GPU 106 may executing instructions stored in filtering module 121 to provide a filtered output signal such that the amplitude of the output does not violate the tube constraint.

The set of filter coefficients may be calculated to model the blunt noise but not the primary component of the signal using, for example, data measured via modeling data acquisition unit 170. When this modeled signal is subtracted from the original signal that is contaminated with the blunt noise, the difference between the filtered signal and the original diagnostic signal is constrained by the ε-tube value. By setting the ε-tube values to the amplitude of the primary component of the original diagnostic signal, ε-tube filtering advantageously prevents estimation errors from affecting regions of the diagnostic signal neighboring the blunt noise. In other words, setting appropriate ε-tube values prevents the calculation of filter coefficients that would result in the primary component of the signal being filtered when the filtering coefficients are applied to the input signal.

The concept of ε-tube may be presented in the form of Vapnik's loss function, which allows for a margin, called the tube, in which the error that is assigned to the points that fall inside the tube is zero. In mathematical terms, Vapnik's loss function may be represented as Eqn. 1 below:

$$|g_t - y_t(U,w)|_\varepsilon = \max(0, |g_t - y_t(U,w)| - \varepsilon) \quad (1)$$

Using system 100 as an example, $g_t$ may represent the value of a signal at time t. This signal may include, for example, the diagnostic signal measured by diagnostic data acquisition unit 150 via one or more electrodes 152.1-152.n. Again, in an embodiment, this diagnostic signal may correspond to an IP signal. Further using system 100 as an example, $y_t$ may represent the output of a filter at a time t implemented by data acquisition system 100 using a calculated set of filter coefficients, U may represent a matrix whose rows are the movement parameter values (e.g., accelerometer signals), w may represent the vector representing the calculated set of filter coefficients, and ε may represent the width of the tube.

In other words, according to Eqn. 1, for points in which the difference between the filtered signal output and the input signal is less than ε (points that fall within the tube) there is a zero error. Furthermore, ε-tube filtering is well-suited to removing blunt noise from a signal that is periodic in nature. This is particularly true given that the amplitude of the primary component of the input signal does not change rapidly over a relatively short period of time (e.g., 1 second) and typically has a regular recurring pattern (e.g., a respiratory component). That is, the main component of an IP signal is respiration, which is periodic and has nearly-constant amplitude within short periods of time. As a result, the ε-tube may be used to estimate the blunt noise while avoiding filter coefficients from being calculated that also model this respiratory component by forming a tube around the IP signal that only encompasses the respiratory component.

In an embodiment, filter module 121 may include instructions, that when executed by CPU 104 and/or GPU 106, causes CPU 104 and/or GPU 106 to implement an ε-tube filter that is formulated as a constrained optimization problem which can be expressed as Eqn. 2 below:

$$\text{Minimize } \Sigma_{t=0}^{N-1} \zeta_t + \Sigma_{t=0}^{N-1} \zeta_t' \quad (2)$$

subject to Eqns. 3-5 below:

$$g_t - y_t(U,w) \leq \varepsilon + \zeta_t, \ t=0,\ldots,N-1, \quad (3)$$

$$y_t(U,w) - g_t \leq \varepsilon + \zeta_t', \ t=0,\ldots,N-1, \quad (4)$$

$$\zeta_t \geq 0 \ \zeta_t' \geq 0, \ t=0,\ldots,N-1, \quad (5)$$

where $\zeta_t$ and $\zeta_t'$ are slack variables that are ideally zero when the filtered signal fits within the tube and grow linearly otherwise, and N is the length of the diagnostic signal over which the filtering is performed, such as a the length of a processing window, for example.

Although data acquisition system 102 may utilize any type of blunt noise modeling process, for example, by CPU 104 and/or GPU 106 executing instructions stored in modeling module 117, an autoregressive exogenous (ARX) model may be preferable due to its flexibility in modeling the blunt noise. An ARX model may be represented by executable instructions stored in modeling module 117 that facilitate the modeling of blunt noise having generic shapes. In an embodiment, the ARX model may be represented as Eqn. 6 below:

$$y_t = -\Sigma_{i=1}^{n_a} a_i y_{t-1} + \Sigma_{i=1}^{n_b} b_i^T u_{t-i+1}, \quad (6)$$

In Eqn. 6, $n_a$, may represent the number of filter poles, while $n_b$, may represent the number of filter zeros plus 1. The number of filter poles and zeroes that are included as part of the executable instructions stored in modeling module 117 may be considered design parameters of the overall filtering process. Thus, these may be varied based upon the particular implementation of system 100, the type of signal that is measured, the sampling rate of the diagnostic signal, the desired error margin of the filtered signal, processing speed, resource limitations, etc.

Further referring back to Eqn. 6 and using the example system 100 as shown in FIG. 1, $a_i$ may represent an i-th feedback coefficient, $u_t$ may represent a vector of movement parameter values (e.g., accelerometer data) at a time t (i.e., a column of U associated with a sample time t) while $b_i$ may represent the corresponding vector of the i-th feedforward coefficients. Therefore, referring back to Eqn. 1, the vector w may be composed of $a_i$'s and the elements of $b_i$'s. Modeling module 117 may include instructions, therefore, that when executed by CPU 104 and/or GPU 106, cause CPU 104 and/or GPU 106 to calculate the vector w that minimizes Eqn. 2 subject to Eqns. 3-5.

However, due to mathematical representation of the ε-tube, the solution for w is unique only when the diagnostic signal is exactly periodic, has a constant amplitude and a regular pattern, and the blunt noise included in the signal is generated through an ARX modeling process. Because these assumptions are unlikely to be true when measuring an actual signal, the calculated solution for w may not be unique, but instead includes a set of filter coefficients that satisfy the minimized constraint of Eqn. 2. This set of filter coefficients also includes those filter coefficients by which the blunt noise has been generated.

FIG. 3A illustrates a graphical representation of an IP signal contaminated with blunt noise and a reference $CO_2$ signal. Again, the embodiments described herein may be applicable to filter any suitable type of periodic diagnostic signal, but an IP signal is shown in FIG. 3A for illustrative purposes. Similar to FIG. 2A, FIG. 3A also shows a $CO_2$ signal in addition to the IP signal for comparative purposes, but the $CO_2$ signal is not needed for the filtering process.

FIG. 3B illustrates a graphical representation of a filtered IP signal after ε-tube filtering. FIG. 3B is an example of the IP signal shown in FIG. 3A being filtered via the application of a set of filter coefficients that satisfy the minimized constraint of Eqn. 2. In other words, the filtered signal as shown in FIG. 3B has an error of zero (i.e., the filtered IP signal output is completely constrained within the ε-tube) and thus the calculated set of filter coefficients represent one set of filter coefficients that satisfy an optimal solution to the minimized constraint of Eqn. 2.

However, the filtered IP signal does not resemble the shape of the respiratory component of the IP signal shown in FIG. 3A, as the calculated set of filter coefficients shown in FIG. 3B yield a filtered output signal containing high frequency noise 302. As a result, embodiments include calculating a set of filter coefficients based upon a second criterion to yield a filter coefficient solution that is most likely to be the generator of the blunt noise. Assuming that the signal follows a regular pattern, such as the pattern corresponding to the patient's respiration, for example, embodiments include utilizing the regularity of the signal as a second objective to maximize. This is shown mathematically in Eqn. 7 below:

$$\text{Minimize } f = \Sigma_{t=0}^{N-1} \zeta_t + \Sigma_{t=0}^{N-1} \zeta_t' - cR(g, U, w), \quad (7)$$

Where g is the vector of contaminated signal values within the processing window, e.g., the IP signal. That is, Eqn. 7 may be implemented as part of the instructions stored in regularization module 119, as shown in FIG. 1. Thus, when executed by CPU 104 and/or GPU 106, instructions stored in regularization module 119 may cause CPU 104 and/or GPU 106 to calculate a set of filter coefficients by selecting, from set of filter coefficients satisfying the minimized constraint of Eqn. 2, the filter coefficients that also satisfy Eqn. 7.

FIG. 3C illustrates a graphical representation of a filtered IP signal after application of ε-tube filtering as shown in FIG. 2B and application of regularization. Additional details of how the instructions stored in regularization module 119 may implement this functionality are further discussed below.

Referring back to Eqn. 7, R(g, U, w) may represent a regularization term, which is discussed further below, while c may represent a design parameter that provides adjustment for a balance between the two objectives. Similar to the number of filter poles and zeroes, the design parameter c may be varied based upon the particular implementation of system 100, processing speed, resource limitations, etc. A suitable value of c depends on the amplitude of the signals, which are in turn based upon the particular test that is being performed. In experimental tests using IP signals having amplitudes on the order of magnitude as those discussed herein, suitable values for c may be 10 or 20, for example. CPU 104 and/or GPU 106 may calculate a set of filter coefficients corresponding to a filtered output signal having the most regular pattern among the filter coefficients solutions that provide the smallest error.

As used herein, a "regular signal" has a frequency composition that is invariant as time progresses. In an embodiment, this property may be determined through the use of a Stockwell transform (S-transform). The S-transform is a generalization of a short time Fourier transform and provides a time-frequency representation of the signal that is sensitive to irregularities in the signal. A discrete time S-Transform may be represented mathematically by Eqns. 8-9 below:

$$S_y\left[pT, \frac{n}{NT}\right] = \sum_{m=0}^{N-1} Y\left[\frac{m+n}{NT}\right] e^{-\frac{2\pi^2 m^2}{n^2}} e^{\frac{j2\pi mp}{N}}, \quad (8)$$

$$n \neq 0$$

and $$S_y\left[pT, \frac{n}{NT}\right] = \frac{1}{N} \sum_{m=0}^{N-1} y\left[\frac{m}{NT}\right], \quad (9)$$

$$n = 0$$

In the above example, Y represents the Fourier transform of y, while p, and n represent the time and frequency indices of the S-transform, respectively. In addition, N represents the number of samples in the signal while T represents the processing window. Furthermore, the inverse S-transform of $S_y$ is defined mathematically by Eqn. 10 below:

$$y[kT] = \frac{1}{N} \sum_{n=0}^{N-1} \sum_{p=0}^{N-1} S_y\left[pT, \frac{n}{NT}\right] e^{\frac{j2\pi nk}{N}} \quad (10)$$

Figure 4A:
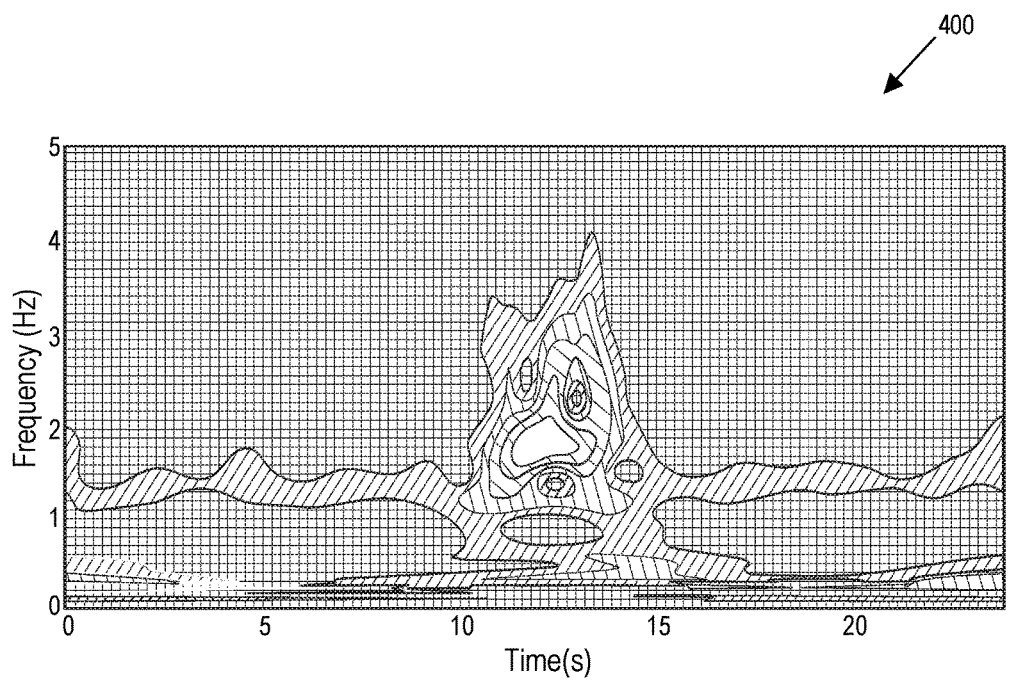
FIG. 4A illustrates a graphical representation of a Stockwell-transform of a filtered IP signal using a set of filter coefficients that satisfy the minimized constraint of Eqn. 2 but without regularization.

FIG. 4A illustrates a graphical representation of a Stockwell-transform of a filtered IP signal using a set of filter coefficients that satisfy the minimized constraint of Eqn. 2 but without regularization. This could include, for example, a signal such as the filtered IP signal shown in FIG. 3B. The S-Transform of an ideal signal with a regular pattern would result in any two given points on the time axis having identical frequency decompositions. Therefore, an average correlation between different vertical "slices" of the S-transform may be used as a measure for the regularity of the signal.

In other words, regularization module 119 may include instructions that allow CPU 104 and/or GPU 106 to perform an S-Transform on one or more of the resulting filtered diagnostic signals, and to analyze the average correlation of frequency compositions at different times within the processing window of the filtered signal. CPU 104 and/or GPU 106 may then select the filter coefficients from those that produced filtered output signals satisfying the minimized constraint of Eqn. 2 and that also produce the most regular (i.e., least time-varying) filtered signal based upon the S-Transform regularity analysis.

In one embodiment, the regularization analysis may be performed through the use of the S-Transform, because S-transforms provide a particular advantage given their sensitivity to signal irregularities. However, in other embodiments, alternative regularization techniques may be implemented, such as an analysis of one or more features extracted from a Fourier transform of the signal, an analysis of signal variance, kurtosis, entropy, an analysis of one or more features extracted from a Wavelet transformation of the signal, etc.

Figure 4B:
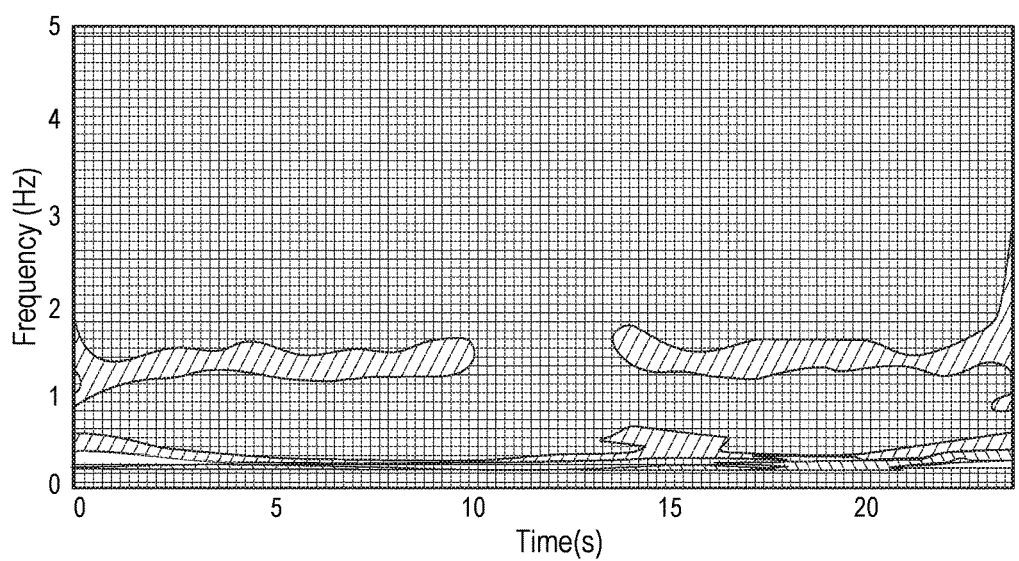
FIG. 4B illustrates a graphical representation of a Stockwell-transform of a filtered IP signal using a set of filter coefficients that satisfy both the minimized constraint of Eqn. 2 after the application of regularization.

FIG. 4B illustrates a graphical representation of a Stockwell-transform of a filtered IP signal using a set of filter coefficients that satisfy both the minimized constraint of Eqn. 2 after the application of regularization. This could include, for example, a signal such as the filtered IP signal shown in FIG. 3C. As shown in FIG. 4B, the resulting frequency decomposition has a nearly constant frequency pattern along the time axis. The white band around f=0.25 Hz corresponds to the respiration component of the IP signal, which is the primary component of the IP signal. The gray band around f=1.3 Hz, however, corresponds to heart rate component that is the secondary component of the IP signal and corresponds to the higher frequency ripple as shown in FIG. 3C.

To satisfy the minimized constraint of Eqn. 2 subject to Eqns. 3-5, modeling module 117 may include one or more instructions to cause CPU 104 and/or GPU 106 to recursively solve Eqn. 6 as indicated by the ARX model. However, to further satisfy the minimized constraint of Eqn. 7 subject to Eqns. 3-5, regularization module 119 may include one or more instructions to cause CPU 104 and/or GPU 106 to calculate and/or evaluate the gradients of the objective function (Eqn. 7) and the constraints (Eqns. 3-5) at one or more sampled times within a processing window. Regularization module 119 may include instructions to facilitate any suitable technique being performed by CPU 104 and/or GPU 106 to determine these calculations. In an embodiment, regularization module 119 may include instructions that facilitate CPU 104 and/or GPU 106 executing one or more of the mathematical steps described in Provisional Patent Application No. 61/912,616 at pages 4-5, the disclosure of which is incorporated herein by reference in its entirety.

Adaptive Versus Non-Adaptive Embodiments

Some of the embodiments described herein discuss the calculation of filter coefficients through the use of ARX modeling of the blunt noise. That is, CPU 104 and/or GPU 106 may execute instructions stored in modeling module 117 to calculate sets of filter coefficients that, when applied to an input signal, result in filtered output signals that satisfy the minimized constraint of Eqn. 2 through the use of an ARX model, such as the ARX model represented in FIG. 6, for example. Again, use of the ARX model may facilitate the calculation of blunt noise models having generic shapes.

ARX models also advantageously allow modeling of the blunt noise through an analysis of past and current sampled values of the modeling data (e.g., movement parameter values) as part of a recursive calculation process, which is illustrated mathematically by Eqn. 6. As a result, ARX modeling may require a large number of calculations and/or processing resources, which may be somewhat time-consuming.

Therefore, although ARX modeling embodiments may be used for both real-time and post-processing embodiments, ARX modeling implementations may be better suited to implementations of system 100 in which a signal is sampled, stored, and the filtering subsequently performed. Furthermore, the processing resources used for ARX modeling may limit its application to real-time filtering, and therefore ARX modeling embodiments may be better suited for non-adaptive filtering embodiments. Non-adaptive filtering embodiments do not change the filter parameters such as the Epsilon value, for example, as the signal is received in real-time. When ARX modeling embodiments are used as part of a post-process filtering, however, adapting the filter to the signal in such a way is less of a concern.

However, for embodiments implementing adaptive filtering techniques, less processor-intensive modeling techniques may be utilized. For example, signals may be filtered according to a series of successively received sliding-time windows. Within each sliding-time windows, the blunt noise may be modeled using sampled values of the modeling data within each sliding-time window (e.g., movement parameter values). Such modeling techniques may be more suitable to filtering signals in real-time, i.e., by processing each sliding-time window as it is received.

Furthermore, adaptive filtering techniques may facilitate the adjustment of filter parameters for each signal as it is received in successive sliding-time windows, thereby adapting to the signal as it is received. For example, new Epsilon values may be changed based on whether the received signal amplitude increases or decreases between successive sliding-time windows. In addition, other filtering processes may be performed on a sliding-time window basis, such as the computation of S-Transforms, for example. Such adaptive filtering may provide additional advantages, for example, such as using more accurate Epsilon values that may be updated when the received signal is uncontaminated with blunt noise.

Figure 5:
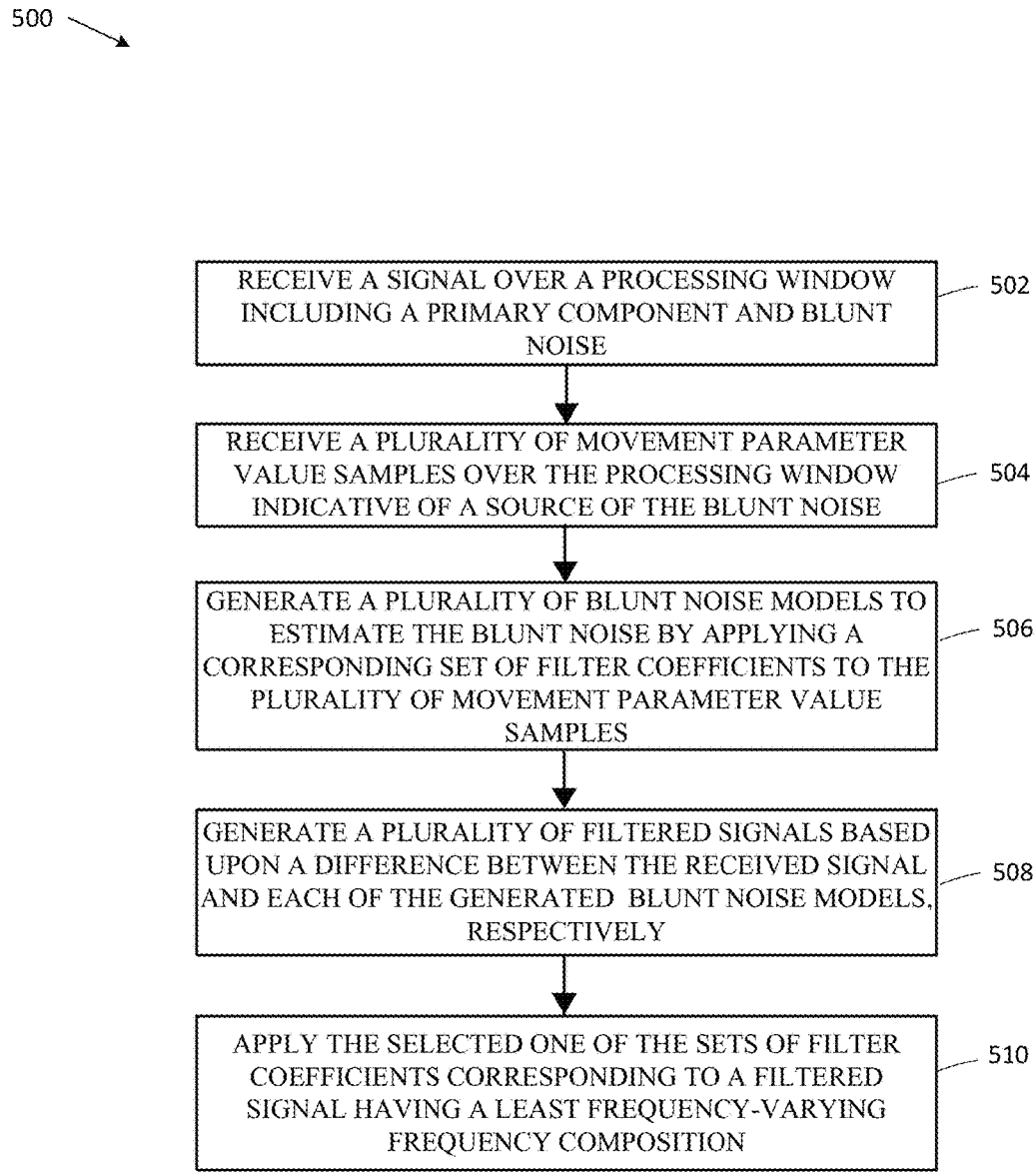
FIG. 5 illustrates an example method 500 in accordance with an exemplary aspect of the present disclosure.

FIG. 5 illustrates an example method 500 in accordance with an exemplary aspect of the present disclosure. In an embodiment, method 500 may be implemented by any suitable computing device, such as data acquisition system 102, for example, as shown in FIG. 1. In an embodiment, method 500 may be performed by one or more processors executing one or more algorithms, applications, programs, and/or routines, such as any suitable portion of CPU 104 and/or GPU 106 executing instructions stored in one or more of data acquisition module 115, modeling module 117, regularization module 119, and/or filtering module 121, for example, as shown in FIG. 1.

Method 500 may start when one or more processors receive a signal over a processing window (block 502). This signal may be received, for example, via communication unit 110 of diagnostic data acquisition unit 150, as shown in FIG. 1 (block 502). In an embodiment, the signal may include a primary signal component and blunt noise. The primary signal component may have an amplitude that varies over time within a maximum and a minimum amplitude. The signal may correspond to any suitable type of signal that may be prone to blunt noise contamination, such as an IP signal, a periodic diagnostic medical signal having a primary component, etc. In the case of an IP signal, this primary component may correspond to the respiratory component of the IP signal.

In some embodiments, the processing window may be any suitable timeframe over which the signal is received (block 502). In such embodiments, the signal may be sampled over the processing window for the subsequent calculation of filter coefficients and filtering of the blunt noise from the signal (block 502). Such embodiments may be particularly useful for batch processing and/or non-adaptive filtering implementations, since larger time intervals may be more efficiently filtered after the signal are received, sampled, and/or processed.

In other embodiments, the processing window may be any suitable sliding timeframe (block 502). In such embodiments, the signal may be sampled over each of the successive sliding windows while filter coefficients are calculated and filtering is performed for each successive sliding window. These embodiments may be particularly useful for real-time and/or adaptive filtering implementations, since the filtering of signals within smaller sliding time windows may be performed in real-time.

Method 500 may include one or more processors receiving a plurality of movement parameter value samples over the processing window indicative of a source of the blunt noise (block 504). The movement parameter value samples may be received, for example, via communication unit 1010 of modeling data acquisition unit 170, as shown in FIG. 1 (block 504). The movement parameter value samples may represent, for example, accelerometer data indicative of a patient's movement causing the blunt noise to be introduced into the received signal (block 502).

Method 500 may include one or more processors generating a plurality of blunt noise models to estimate the blunt noise (block 506). In an embodiment, the blunt noise models may be generated by the one or more processors by applying, for each blunt noise model from among the plurality of blunt noise models, a corresponding set of filter coefficients to the plurality of movement parameter value samples (block 506). In an embodiment, the blunt noise models may be calculated using any suitable modeling technique, such as an ARX model or a moving average model, for example (block 506). As previously discussed above, ARX modeling may be particularly well-suited to non-adaptive filtering embodiments, while moving average models may be better suited to adaptive, real-time filtering embodiments.

Method 500 may include one or more processors generating a plurality of filtered signals based upon a difference between the received signal (block 502) and each generated blunt noise model (block 506) from among the plurality of blunt noise models (block 508).

To further narrow the number of calculated filter coefficients generated by method 500, however, method 500 may continue (block 510) to determine which of the calculated filter coefficients result in filtered signals having an amplitude less than the amplitude of the original, unfiltered signal (block 510). In an embodiment, this may include the minimized constraint of solution of eqn. 2 subject to Eqns. 3-5 (block 510). Thus, as part of the filter coefficient calculation process, only those filter coefficients that result in filtered signals satisfying the Epsilon constraint may be retained as part of a possible set of filter coefficient solutions (block 508), while those that do not satisfy the Epsilon constraint may be discarded or otherwise not used as part of an optimal filter coefficient solution. An example of one of these filtered signals that satisfies the Epsilon constraint is shown in FIG. 3B.

Method 500 may include one or more processors applying the selected set of filter coefficients having a frequency composition that is the least frequency-varying of the plurality of filtered signals (block 508) that satisfy the Epsilon constraint (block 510). In an embodiment, this may include, for example, regularization in accordance with a mathematical solution to the minimized constraint of Eqn. 7 subject to Eqns. 3-5 (block 510). In an embodiment, this regularization may be performed using any suitable type of frequency transform algorithm, such as the S-Transform, for example. An example of an application of the selected set of filter coefficients to a signal that satisfy the Epsilon constraint (block 508) and provide a filtered signal that is the least frequency-varying of the filtered signals (block 510) is shown in FIG. 3C.

As shown in FIG. 3C, for example, upon filtering the signal using the selected set of filter coefficients, the filtered signal may retain the primary signal component while removing the blunt noise (block 510). In various embodiments, method 500 may perform one or more of the filter coefficient calculation and/or selection processes in any order suitable for the calculation of the optimal filter coefficient solution. For example, the processes represented in one or more of blocks 506, 508, and/or 510 may be performed concurrently or in a particular sequence with respect to one another.

Embodiments of the present disclosure relate to one or more of the following clauses.

In a first embodiment, a computer-implemented method is performed by one or more processors to filter a signal and includes (1) receiving, by one or more processors, a signal over a processing window, the signal including a primary signal component and blunt noise, the primary signal component having an amplitude that varies between a maximum and minimum amplitude; (2) receiving, by one or more processors, a plurality of movement parameter value samples over the processing window, the plurality of movement parameter value samples being indicative of a source of the blunt noise; (3) generating, by one or more processors, a plurality of blunt noise models to estimate the blunt noise by applying a corresponding set of filter coefficients to the plurality of movement parameter value samples; and (4) generating, by one or more processors, a plurality of filtered signals based upon a difference between the signal and each respective blunt noise model from among the plurality of blunt noise models by (i) selecting sets of filter coefficients corresponding to ones of the plurality of blunt noise models that generate corresponding filtered signals having amplitudes that vary between the maximum and minimum amplitude; and (ii) filtering the signal by applying one of the sets of filter coefficients corresponding to a blunt noise model from among the plurality of blunt noise models that, when used to generate a corresponding filtered signal from among the plurality of filtered signals, has a frequency composition that is the least frequency-varying of the plurality of filtered signals within the processing window to retain the primary signal component while removing the blunt noise.

Variations of the first and other embodiments include the signal corresponding to an impedance plethysmography (IP) signal, the primary signal component corresponds to a respiratory component of the IP signal, the blunt noise corresponds to an artifact introduced into the IP signal due to a person's movement, and the blunt noise having a peak amplitude that is greater than the maximum amplitude.

Variations of the first and other embodiments additionally include the act of generating the plurality of filtered signals including minimizing a constrained optimization equation:

$$\Sigma_{t=0}^{N-1}\zeta_t + \Sigma_{t=0}^{N-1}\zeta_t' - cR(g,U,w), \text{ wherein:}$$

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and R (g, U, w) is a regularity term that is maximized when a set of filter coefficients result in a filtered signal with the least frequency-varying spectrum, and the constrained optimization equation is subject to:

$$g_t - y_t(U,w) \leq \varepsilon + \zeta_t, \quad t=0, \ldots, N-1,$$

$$y_t(U,w) - g_t \leq \varepsilon + \zeta_t', \quad t=0, \ldots, N-1,$$

$$\zeta_t \geq 0, \zeta_t' \geq 0, \quad t=0, \ldots, N-1,$$

wherein $g_t$ represents a value of the signal at a sampling time t within the processing window, and wherein $y_t$ (U,w) represents one of the plurality of blunt noise models.

Variations of the first and other embodiments further include the movement parameter value samples corresponding to accelerometer values in the x, y, and z-axes, and U representing a matrix having a number of columns corresponding to each of the plurality of samples over the processing window and a number of rows corresponding to each of the accelerometer values in the x, y, and z-axes.

Variations of the first and other embodiments also include generating the plurality of blunt noise models by generating an autoregressive exogenous model according to the equation:

$$y_t = \Sigma_{i=1}^{n_a} a_i y_{t-i} + \Sigma_{i=1}^{n_b} u_{t-i+1}, \text{wherein:}$$

$y_t$ is equal to a value of one of the plurality of filtered signals at a sampling time t within the processing window, $n_a$ is equal to a number of filter poles, $n_b$ is equal to a number of filter zeroes plus one, $a_i$ is a i-th feedback coefficient from among the corresponding set of filter coefficients, $b_i$ is a i-th feedforward coefficient set from among the corresponding set of filter coefficients, $u_t$ is a vector including the x, y, and z-axis accelerometer values at a sampling time t within the processing window, and wherein w represents a vector that minimizes the constrained optimization equation and includes feedback coefficients and feedforward coefficients from among the corresponding set of filter coefficients.

Variations of the first and other embodiments also include selecting one of the sets of filter coefficients by (1) calculating a Stockwell transform of each of the plurality of filtered signals to generate a plurality of respective filtered signal frequency decompositions; (2) calculating, for each of the filtered signal frequency decompositions, an average correlation between frequency components over a plurality of samples within the processing window; and (3) determining, by one or more processors, which of the plurality of filtered signals has a frequency composition that is the least frequency-varying based upon the average correlation of between frequency components for each of the filtered signal frequency decompositions.

Variations of the first and other embodiments also include the signal being filtered in real-time as the signal is received and/or the signal being filtered as part of a batch processing after the signal is received.

Variations of the first and other embodiments also include the signal including one or more of an electrocardiogram, an impedance cardiograph, an impedance-based blood volume waveform, an arterial blood pressure waveform, a venous blood pressure waveform, an intracranial pressure waveform, a photoplethysmography waveform, an end-tidal carbon dioxide waveform, a Doppler signal, and/or a piezoelectric signal.

In a second embodiment, a data acquisition system is disclosed that is configured to filter a signal by (1) receiving the signal over a processing window, the signal including a primary signal component and blunt noise, the primary signal component having an amplitude that varies between a maximum and minimum amplitude; (2) receiving a plurality of movement parameter value samples over the processing window, the plurality of movement parameter value samples being indicative of a source of the blunt noise; (3) generating a plurality of blunt noise models to estimate the blunt noise by applying a corresponding set of filter coefficients to the plurality of movement parameter value samples; and (4) generating a plurality of filtered signals based upon a difference between the signal and each respective blunt noise model from among the plurality of blunt noise models by (i) selecting sets of filter coefficients corresponding to ones of the plurality of blunt noise models that generate corresponding filtered signals having amplitudes that vary between the maximum and minimum amplitude; and (ii) filtering the signal by applying one of the sets of filter coefficients corresponding to a blunt noise model from among the plurality of blunt noise models that, when used to generate a corresponding filtered signal from among the plurality of filtered signals, has a frequency composition that is the least frequency-varying of the plurality of filtered signals within the processing window to retain the primary signal component while removing the blunt noise.

Variations of the second and other embodiments include the signal corresponding to an impedance plethysmography (IP) signal, the primary signal component corresponds to a respiratory component of the IP signal, the blunt noise corresponds to an artifact introduced into the IP signal due to a person's movement, and the blunt noise having a peak amplitude that is greater than the maximum amplitude.

Variations of the second and other embodiments additionally include the data acquisition system generating the plurality of filtered signals including minimizing a constrained optimization equation:

$$\Sigma_{t=0}^{N-1} \zeta_t + \Sigma_{t=0}^{N-1} \zeta_t' - cR(g, U, w), \text{ wherein:}$$

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and R (g, U, w) is a regularity term that is maximized when a set of filter coefficients result in a filtered signal with the least frequency-varying spectrum, and the constrained optimization equation is subject to:

$$g_t - y_t(U, w) \leq \varepsilon + \zeta_t, \ t = 0, \ldots, N-1,$$

$$y_t(U, w) - g_t \leq \varepsilon + \zeta_t', \ t = 0, \ldots, N-1,$$

$$\zeta_t \geq 0, \zeta_t' \geq 0, t = 0, \ldots, N-1,$$

wherein $g_t$ represents a value of the signal at a sampling time t within the processing window, and wherein $y_t$ (U,w) represents one of the plurality of blunt noise models.

Variations of the second and other embodiments further include the movement parameter value samples corresponding to accelerometer values in the x, y, and z-axes, and U representing a matrix having a number of columns corresponding to each of the plurality of samples over the processing window and a number of rows corresponding to each of the accelerometer values in the x, y, and z-axes.

Variations of the second and other embodiments also include the data acquisition system generating the plurality of blunt noise models by generating an autoregressive exogenous model according to the equation:

$$y_t = -\Sigma_{i=1}^{n_a} a_i y_{t-i} + \Sigma_{i=1}^{n_b} b_i^T u_{t-i+1}, \text{ wherein:}$$

$y_t$ is equal to a value of one of the plurality of filtered signals at a sampling time t within the processing window, $n_a$ is equal to a number of filter poles, $n_b$ is equal to a number of filter zeroes plus one, $a_i$ is a i-th feedback coefficient from among the corresponding set of filter coefficients, $b_i$ is a i-th feedforward coefficient set from among the corresponding set of filter coefficients, $u_t$ is a vector including the x, y, and z-axis accelerometer values at a sampling time t within the processing window, and wherein w represents a vector that minimizes the constrained optimization equation and includes feedback coefficients and feedforward coefficients from among the corresponding set of filter coefficients.

Variations of the second and other embodiments also include the data acquisition system selecting one of the sets of filter coefficients by (1) calculating a Stockwell transform of each of the plurality of filtered signals to generate a plurality of respective filtered signal frequency decompositions; (2) calculating, for each of the filtered signal frequency decompositions, an average correlation between frequency components over a plurality of samples within the processing window; and (3) determining, by one or more processors, which of the plurality of filtered signals has a frequency composition that is the least frequency-varying based upon the average correlation of between frequency components for each of the filtered signal frequency decompositions.

Variations of the second and other embodiments also include the data acquisition system filtering the signal in real-time as the signal is received and/or filtering the signal as part of a batch processing after the signal is received.

Variations of the second and other embodiments also include the signal including one or more of an electrocardiogram, an impedance cardiograph, an impedance-based blood volume waveform, an arterial blood pressure waveform, a venous blood pressure waveform, an intracranial pressure waveform, a photoplethysmography waveform, an end-tidal carbon dioxide waveform, a Doppler signal, and/or a piezoelectric signal.

In a third embodiment, a non-transitory computer readable media having instructions stored thereon in a data acquisition device is executed by a processor to cause the processor to (1) receive a signal over a processing window, the signal including a primary signal component and blunt noise, the primary signal component having an amplitude that varies between a maximum and minimum amplitude; (2) receive a plurality of movement parameter value samples over the processing window, the plurality of movement parameter value samples being indicative of a source of the blunt noise; (3) generate a plurality of blunt noise models to estimate the blunt noise by applying a corresponding set of filter coefficients to the plurality of movement parameter value samples; and (4) generate a plurality of filtered signals based upon a difference between the signal and each respective blunt noise model from among the plurality of blunt noise models by (i) selecting sets of filter coefficients corresponding to ones of the plurality of blunt noise models that generate corresponding filtered signals having amplitudes that vary between the maximum and minimum amplitude; and (ii) filtering the signal by applying one of the sets of filter coefficients corresponding to a blunt noise model from among the plurality of blunt noise models that, when used to generate a corresponding filtered signal from among the plurality of filtered signals, has a frequency composition that is the least frequency-varying of the plurality of filtered signals within the processing window to retain the primary signal component while removing the blunt noise.

Variations of the third and other embodiments include the signal corresponding to an impedance plethysmography (IP) signal, the primary signal component corresponds to a respiratory component of the IP signal, the blunt noise corresponds to an artifact introduced into the IP signal due to a person's movement, and the blunt noise having a peak amplitude that is greater than the maximum amplitude.

Variations of the third and other embodiments additionally the instructions being executed by a processor to cause the processor to generate the plurality of filtered signals including minimizing a constrained optimization equation:

$$\Sigma_{t=0}^{N-1}\zeta_t + \Sigma_{t=0}^{N-1}\zeta_t' - cR(g,U,w),\text{ wherein:}$$

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and R (g, U, w) is a regularity term that is maximized when a set of filter coefficients result in a filtered signal with the least frequency-varying spectrum, and the constrained optimization equation is subject to:

$$g_t - y_t(U,w) \le \varepsilon + \zeta_t, \ t=0,\ldots,N-1,$$

$$y_t(U,w) - g_t \le \varepsilon \zeta_t', \ t=0,\ldots,N-1,$$

$$\zeta_t \ge 0, \ \zeta_t' \ge 0, \ t=0,\ldots,N-1,$$

wherein $g_t$ represents a value of the signal at a sampling time t within the processing window, and wherein $y_t(U,w)$ represents one of the plurality of blunt noise models.

Variations of the third and other embodiments further include the movement parameter value samples corresponding to accelerometer values in the x, y, and z-axes, and U representing a matrix having a number of columns corresponding to each of the plurality of samples over the processing window and a number of rows corresponding to each of the accelerometer values in the x, y, and z-axes.

Variations of the third and other embodiments also include the instructions being executed by a processor to cause the processor to generate the plurality of blunt noise models by generating an autoregressive exogenous model according to the equation:

$$y_t = -\Sigma_{i=1}^{n_a} a_i y_{t-1} + \Sigma_{i=1}^{n_b} b_i^T u_{t-i+1}, \text{ wherein:}$$

$y_t$ is equal to a value of one of the plurality of filtered signals at a sampling time t within the processing window, $n_a$ is equal to a number of filter poles, $n_b$ is equal to a number of filter zeroes plus one, $a_i$ is a i-th feedback coefficient from among the corresponding set of filter coefficients, $b_i$ is a i-th feedforward coefficient set from among the corresponding set of filter coefficients, $u_t$ is a vector including the x, y, and z-axis accelerometer values at a sampling time t within the processing window, and wherein w represents a vector that minimizes the constrained optimization equation and includes feedback coefficients and feedforward coefficients from among the corresponding set of filter coefficients.

Variations of the third and other embodiments also include the instructions being executed by a processor to cause the processor to select one of the sets of filter coefficients by (1) calculating a Stockwell transform of each of the plurality of filtered signals to generate a plurality of respective filtered signal frequency decompositions; (2) calculating, for each of the filtered signal frequency decompositions, an average correlation between frequency components over a plurality of samples within the processing window; and (3) determining, by one or more processors, which of the plurality of filtered signals has a frequency composition that is the least frequency-varying based upon the average correlation of between frequency components for each of the filtered signal frequency decompositions.

Variations of the third and other embodiments also include the instructions being executed by a processor to cause the processor to filter the signal in real-time as the signal is received and/or to filter the signal as part of a batch processing after the signal is received.

Variations of the third and other embodiments also include the signal including one or more of an electrocardiogram, an impedance cardiograph, an impedance-based blood volume waveform, an arterial blood pressure waveform, a venous blood pressure waveform, an intracranial pressure waveform, a photoplethysmography waveform, an end-tidal carbon dioxide waveform, a Doppler signal, and/or a piezoelectric signal.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component.

Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method of filtering a diagnostic signal indicative of a physical measurement comprising:
    receiving, by one or more processors as a result of execution of instructions stored in a data acquisition module in memory, a diagnostic signal from a diagnostic data acquisition unit over a processing window representing a timeframe, the diagnostic signal including a primary signal component and blunt noise, the primary signal component having an amplitude that varies between a maximum and minimum amplitude;
    receiving, by one or more processors as a result of execution of instructions stored in the data acquisition module, a plurality of movement parameter value samples over the processing window from a modeling data acquisition unit, the plurality of movement parameter value samples being indicative of a user's physical movement causing the blunt noise to be introduced into the received diagnostic signal as a motion artifact having a frequency spectrum that overlaps with the received diagnostic signal;
    generating, by one or more processors as a result of execution of instructions stored in a modeling module in memory, a plurality of blunt noise models to estimate the blunt noise by applying a corresponding set of filter coefficients to the plurality of movement parameter value samples to generate each blunt noise model from among the plurality of blunt noise models;
    generating, by one or more processors, a plurality of filtered signals based upon a difference between the diagnostic signal and each respective blunt noise model from among the plurality of blunt noise models by:
        (i) selecting, as a result of execution of instructions stored in a regularization module in memory, sets of filter coefficients corresponding to a subset of the plurality of blunt noise models that, when used to generate a corresponding filtered signal from among the plurality of filtered signals, results in the generation of corresponding filtered signals having amplitudes that are bound between the maximum and minimum amplitude of the diagnostic signal's primary signal component within the processing window in accordance with an Epsilon tube ($\varepsilon$-tube) constraint; and
        (ii) filtering, as a result of execution of instructions stored in a filtering module in memory, the diagnostic signal to provide a filtered signal by applying one of the sets of filter coefficients corresponding to a blunt noise model from among the subset of the plurality of blunt noise models that, when used to generate a corresponding filtered signal from among the plurality of filtered signals, has a frequency composition that has the least frequency-varying spectrum within the processing window to retain the primary signal component while removing the blunt noise; and
    displaying, by one or more processors as a result of execution of instructions stored in the filtering module, the filtered signal, wherein the diagnostic signal includes one or more of the following;
    an electrocardiogram;
    an impedance cardiograph;
    an impedance-based blood volume waveform;
    an arterial blood pressure waveform;
    a venous blood pressure waveform;
    an intracranial pressure waveform;
    a photoplethysmography waveform;
    an end-tidal carbon dioxide waveform;
    a Doppler signal; and
    a piezoelectric signal.

2. The computer-implemented method of claim 1, wherein:
    the diagnostic signal corresponds to an impedance plethysmography (IP) signal,
    the primary signal component corresponds to a respiratory component of the IP signal, and
    the blunt noise has a peak amplitude that is greater than the maximum amplitude.

3. The computer-implemented method of claim 1, wherein the act of generating the plurality of filtered signals comprises:
    minimizing a constrained optimization equation:

$\Sigma_{t=0}^{N-1} \zeta_t + \Sigma_{t=0}^{N-1} \zeta_t' - cR(g, U, w)$, wherein:

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and $R(g,U,w)$ is a regularity term that is maximized when a set of filter coefficients result in a filtered signal with the least frequency-varying spectrum, and
    the constrained optimization equation is subject to:

$$g_t - y_t(U,w) \leq \varepsilon + \zeta_t,\ t=0,\ldots,N-1, \qquad (3)$$

$$y_t(U,w) - g_t \leq \varepsilon + \zeta_t',\ t=0,\ldots,N-1, \qquad (4)$$

$$\zeta_t \geq 0,\ \zeta_t' \geq 0,\ t=0,\ldots,N-1, \qquad (5)$$

wherein $g_t$ represents a value of the diagnostic signal at a sampling time t within the processing window, and
    wherein $y_t(U,w)$ represents one of the plurality of blunt noise models.

4. The computer-implemented method of claim 3, wherein:
    the movement parameter value samples correspond to accelerometer values in the x, y, and z-axes, and
    U represents a matrix having a number of columns corresponding to each of the plurality of samples over the processing window and a number of rows corresponding to each of the accelerometer values in the x, y, and z-axes.

5. The computer-implemented method of claim 4, and wherein the act of generating the plurality of blunt noise models comprises:

generating an autoregressive exogenous model according to the equation:

$$y_t = \sum_{i=1}^{n_a} a_i y_{t-i} + \sum_{i=1}^{n_b} b_i u_{t-i+1}, \text{wherein:}$$

$y_t$ is equal to a value of one of the plurality of filtered signals at a sampling time t within the processing window, $n_a$ is equal to a number of filter poles, $n_b$ is equal to a number of filter zeroes plus one, $a_i$ is a i-th feedback coefficient from among the corresponding set of filter coefficients, $b_i$ is a i-th feedforward coefficient set from among the corresponding set of filter coefficients, $u_t$ is a vector including the x, y, and z-axis accelerometer values at a sampling time t within the processing window, and wherein w represents a vector that minimizes the constrained optimization equation and includes feedback coefficients and feedforward coefficients from among the corresponding set of filter coefficients.

6. The computer-implemented method of claim 1, wherein the act of selecting one of the sets of filter coefficients comprises:

calculating a Stockwell transform of each of the plurality of filtered signals to generate a plurality of respective filtered signal frequency decompositions;

calculating, for each of the filtered signal frequency decompositions, an average correlation between frequency components over a plurality of samples within the processing window; and determining, by one or more processors, which of the plurality of filtered signals has a frequency composition that is the least frequency-varying based upon the average correlation of between frequency components for each of the filtered signal frequency decompositions.

7. The computer-implemented method of claim 1, wherein the diagnostic signal is filtered in real-time as the diagnostic signal is received.

8. The computer-implemented method of claim 1, wherein the diagnostic signal is filtered as part of a batch processing after the diagnostic signal is received.

9. A data acquisition system to filter a diagnostic signal indicative of a physical measurement, comprising:

a communication unit configured to:

receive a diagnostic signal over a processing window representing a timeframe, the diagnostic signal including a primary signal component and blunt noise, the primary signal component having an amplitude that varies between a maximum and minimum amplitude;

receive a plurality of movement parameter value samples over the processing window, the plurality of movement parameter value samples being indicative of a user's physical movement causing the blunt noise to be introduced into the received diagnostic signal as a motion artifact having a frequency spectrum that overlaps with the received diagnostic signal; and a central processing unit (CPU) configured to:

generate a plurality of blunt noise models to estimate the blunt noise by applying, for each blunt noise model from among the plurality of blunt noise models, a corresponding set of filter coefficients to the plurality of movement parameter value samples;

generate a plurality of filtered signals based upon a difference between the diagnostic signal and each respective blunt noise model from among the plurality of blunt noise models by:

(i) selecting sets of filter coefficients corresponding to a subset of the plurality of blunt noise models that, when used to generate a corresponding filtered signal from among the plurality of filtered signals, results in the generation of corresponding filtered signals having amplitudes that are bound between the maximum and minimum amplitude of the diagnostic signal's primary signal component within the processing window in accordance with an Epsilon tube (ε-tube) constraint; and (ii) filtering the diagnostic signal to provide a filtered signal by applying one of the sets of filter coefficients corresponding to a blunt noise model from among the subset of the plurality of blunt noise models that, when used to generate a corresponding filtered signal from among the plurality of filtered signals, has a frequency composition that has the least frequency-varying spectrum within the processing window to retain the primary signal component while removing the blunt noise; and display the filtered signal, wherein the diagnostic signal includes one or more of the following:

an electrocardiogram;

an impedance cardiograph;

an impedance-based blood volume waveform;

an arterial blood pressure waveform;

a venous blood pressure waveform;

an intracranial pressure waveform;

a photoplethysmography waveform;

an end-tidal carbon dioxide waveform;

a Doppler signal; and a piezoelectric signal.

10. The data acquisition system of claim 9, wherein:

the diagnostic signal corresponds to an impedance plethysmography (IP) signal, the primary signal component corresponds to a respiratory component of the IP signal, and the blunt noise has a peak amplitude that is greater than the maximum amplitude.

11. The data acquisition system of claim 9, wherein the CPU is further configured to generate the plurality of filtered signals by:

minimizing a constrained optimization equation:

$$\sum_{t=0}^{N-1} \zeta_t + \sum_{t=0}^{N-1} \zeta_t' - cR(g, U, w), \text{ wherein:}$$

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and R(g,U,w) is a regularity term that is maximized when a set of filter coefficients result in a filtered signal with the least frequency-varying spectrum, and the constrained optimization equation is subject to:

$$g_t - y_t(U, w) \leq \varepsilon + \zeta_t, \quad t = 0, \ldots, N-1, \tag{3}$$

$$y_t(U, w) - g_t \leq \varepsilon + \zeta_t', \quad t = 0, \ldots, N-1, \tag{4}$$

$$\zeta_t \geq 0, \zeta_t' \geq 0, \quad t = 0, \ldots, N-1, \tag{5}$$

wherein $g_t$ represents a value of the diagnostic signal at a sampling time t within the processing window, and wherein $y_t(U,w)$ represents one of the plurality of blunt noise models.

12. The data acquisition system of claim 11, wherein:

the movement parameter value samples correspond to accelerometer values in the x, y, and z-axes, and U represents a matrix having a number of columns corresponding to each of the plurality of samples over the processing window and a number of rows corresponding to each of the accelerometer values in the x, y, and z-axes.

13. The data acquisition system of claim 12, wherein the CPU is further configured to generate the plurality of blunt noise models by:

generating an autoregressive exogenous model according to the equation:

$$y_t = \Sigma_{i=1}^{n_a} a_i y_{t-i} + \Sigma_{i=1}^{n_b} u_{t-i+1}, \text{wherein:}$$

$y_t$ is equal to a value of one of the plurality of filtered signals at a sampling time t within the processing window, $n_a$ is equal to a number of filter poles, $n_b$ is equal to a number of filter zeroes plus one, $a_i$ is a i-th feedback coefficient from among the corresponding set of filter coefficients, $b_i$ is a i-th feedforward coefficient set from among the corresponding set of filter coefficients, $u_t$ is a vector including the x, y, and z-axis accelerometer values at a sampling time t within the processing window, and wherein w represents a vector that minimizes the constrained optimization equation and includes feedback coefficients and feedforward coefficients from among the corresponding set of filter coefficients.

14. The data acquisition system of claim 9, wherein the CPU is further configured to select one of the sets of filter coefficients by:

calculating a Stockwell transform of each of the plurality of filtered signals to generate a plurality of respective filtered signal frequency decompositions;

calculating, for each of the filtered signal frequency decompositions, an average correlation between frequency components over a plurality of samples within the processing window; and determining which of the plurality of filtered signals has a frequency composition that is the least frequency-varying based upon the average correlation of between frequency components for each of the filtered signal frequency decompositions.

15. The data acquisition system of claim 9, wherein the CPU is further configured to filter the diagnostic signal in real-time as the diagnostic signal is received.

16. The data acquisition system of claim 9, wherein the CPU is further configured to filter the diagnostic signal as part of a batch process after the diagnostic signal is received.

17. A non-transitory, tangible computer-readable medium storing machine readable instructions for filtering a diagnostic signal indicative of a physical measurement that, when executed by a processor, cause the processor to:

receive a diagnostic signal over a processing window representing a timeframe, the diagnostic signal including a primary signal component and blunt noise, the primary signal component having an amplitude that varies between a maximum and minimum amplitude;

receive a plurality of movement parameter value samples over the processing window, the plurality of movement parameter value samples being indicative of a user's physical movement causing the blunt noise to be introduced into the received diagnostic signal as a motion artifact having a frequency spectrum that overlaps with the received diagnostic signal;

generate a plurality of blunt noise models to estimate the blunt noise by applying, for each blunt noise model from among the plurality of blunt noise models, a corresponding set of filter coefficients to the plurality of movement parameter value samples;

generate a plurality of filtered signals based upon a difference between the diagnostic signal and each respective blunt noise model from among the plurality of blunt noise models by:

(i) selecting sets of filter coefficients corresponding to a subset of the plurality of blunt noise models that, when used to generate a corresponding filtered signal from among the plurality of filtered signals, results in the generation of corresponding filtered signals having amplitudes that are bound between the maximum and minimum amplitude of the diagnostic signal's primary signal component within the processing window in accordance with an Epsilon tube ($\varepsilon$-tube) constraint; and (ii) filtering the diagnostic signal to provide a filtered signal by applying one of the sets of filter coefficients corresponding to a blunt noise model from among the subset of the plurality of blunt noise models that, when used to generate a corresponding filtered signal from among the plurality of filtered signals, has a frequency composition that has the least frequency-varying spectrum within the processing window to retain the primary signal component while removing the blunt noise; and display the filtered signal, wherein the diagnostic signal includes one or more of the following:

an electrocardiogram;

an impedance cardiograph;

an impedance-based blood volume waveform;

an arterial blood pressure waveform;

a venous blood pressure waveform;

an intracranial pressure waveform;

a photoplethysmography waveform;

an end-tidal carbon dioxide waveform;

a Doppler signal; and a piezoelectric signal.

18. The non-transitory, tangible computer-readable medium of claim 17, wherein:

the diagnostic signal corresponds to an impedance plethysmography (IP) signal, the primary signal component corresponds to a respiratory component of the IP signal, and the blunt noise has a peak amplitude that is greater than the maximum amplitude.

19. The non-transitory, tangible computer-readable medium of claim 17, wherein the instructions to generate the plurality of filtered signals include instructions that cause the processor to:

minimize a constrained optimization equation:

$$\Sigma_{t=0}^{N-1} \zeta_t + \Sigma_{t=0}^{N-1} \zeta_t' - cR(g,U,w), \text{wherein:}$$

N is the length of the processing window, $\zeta_t$ and $\zeta_t'$ are slack variables, c is a design parameter, g is a vector that contains contaminated signal values within the processing window, U is a matrix whose rows are the input signals values, w is a vector of filter coefficients, and $R(g,U,w)$ is a regularity term that is maximized when a set of filter coefficients result in a filtered signal with the least frequency-varying spectrum, and
the constrained optimization equation is subject to:

$$g_t - y_t(U,w) \leq \varepsilon + \zeta_t, \; t=0, \ldots, N-1, \quad (3)$$

$$y_t(U,w) - g_t \leq \varepsilon + \zeta'_t, \; t=0, \ldots, N-1, \quad (4)$$

$$\zeta_t \geq 0, \zeta'_t \geq 0, \; t=0, \ldots, N-1, \quad (5)$$

wherein $g_t$ represents a value of the diagnostic signal at a sampling time t within the processing window, and
wherein $y_t(U,w)$ represents one of the plurality of blunt noise models.

20. The non-transitory, tangible computer-readable medium of claim 19, wherein:
the movement parameter value samples correspond to accelerometer values in the x, y, and z-axes, and
U represents a matrix having a number of columns corresponding to each of the plurality of samples over the processing window and a number of rows corresponding to each of the accelerometer values in the x, y, and z-axes.

21. The non-transitory, tangible computer-readable medium of claim 20, wherein the instructions to generate the plurality of blunt noise models include instructions that cause the processor to:
generate an autoregressive exogenous model according to the equation:

$$y_t = \sum_{i=1}^{n_a} a_i y_{t-i} + \sum_{i=1}^{n_b} u_{t-i+1}, \text{wherein:}$$

$y_t$ is equal to a value of one of the plurality of filtered signals at a sampling time t within the processing window,
$n_a$ is equal to a number of filter poles,
$n_b$ is equal to a number of filter zeroes plus one,
$a_i$ is a i-th feedback coefficient from among the corresponding set of filter coefficients,
$b_i$ is a i-th feedforward coefficient set from among the corresponding set of filter coefficients,
$u_t$ is a vector including the x, y, and z-axis accelerometer values at a sampling time t within the processing window, and
wherein w represents a vector that minimizes the constrained optimization equation and includes feedback coefficients and feedforward coefficients from among the corresponding set of filter coefficients.

22. The non-transitory, tangible computer-readable medium of claim 17, wherein the instructions to select one of the sets of filter coefficients include instructions that cause the processor to:
calculate a Stockwell transform of each of the plurality of filtered signals to generate a plurality of respective filtered signal frequency decompositions;
calculate, for each of the filtered signal frequency decompositions, an average correlation between frequency components over a plurality of samples within the processing window; and
determine which of the plurality of filtered signals has a frequency composition that is the least frequency-varying based upon the average correlation of between frequency components for each of the filtered signal frequency decompositions.

23. The non-transitory, tangible computer-readable medium of claim 17, wherein the diagnostic signal is filtered in real-time as the signal is received.

24. The non-transitory, tangible computer-readable medium of claim 17, wherein the diagnostic signal is filtered as part of a batch processing after the diagnostic signal is received.

* * * * *

UNITED STATES PATENT AND TRADEMARK OFFICE
CERTIFICATE OF CORRECTION

PATENT NO. : 10,349,896 B2
APPLICATION NO. : 14/563694
DATED : July 16, 2019
INVENTOR(S) : Sardar Ansari et al.

It is certified that error appears in the above-identified patent and that said Letters Patent is hereby corrected as shown below:

On the Title Page

Item (73), Line 2, "UNIVERSTIY" should be -- UNIVERSITY --.

In the Claims

At Column 24, Line 14, "following;" should be -- following: --.

At Column 25, Line 7, "$y_t = \Sigma_{i=1}^{n_a} a_i y_{t-i} + \Sigma_{i=1}^{n_b} u_{t-i+1}$, wherein:" should be -- $y_t = -\sum_{i=1}^{n_a} a_i y_{t-i} + \sum_{i=1}^{n_b} b_i^T u_{t-i+1}$, wherein: --.

At Column 27, Line 19, "$y_t = \Sigma_{i=1}^{n_a} a_i y_{t-i} + \Sigma_{i=1}^{n_b} u_{t-i+1}$, wherein:" should be -- $y_t = -\sum_{i=1}^{n_a} a_i y_{t-i} + \sum_{i=1}^{n_b} b_i^T u_{t-i+1}$, wherein: --.

At Column 29, Line 30, "$y_t = \Sigma_{i=1}^{n_a} a_i y_{t-i} + \Sigma_{i=1}^{n_b} u_{t-i+1}$, wherein:" should be -- $y_t = -\sum_{i=1}^{n_a} a_i y_{t-i} + \sum_{i=1}^{n_b} b_i^T u_{t-i+1}$, wherein: --.

Signed and Sealed this
Thirty-first Day of March, 2020

Andrei Iancu
*Director of the United States Patent and Trademark Office*